United States Patent
Karpman et al.

(10) Patent No.: US 11,896,556 B1
(45) Date of Patent: Feb. 13, 2024

(54) APPARATUS AND METHOD FOR DISPENSING MEDICATION

(71) Applicant: Geri-Safe, LTD., Ithaca, NY (US)

(72) Inventors: Robert Karpman, Ithaca, NY (US); Paula Rose Aronson, Fitchburg, WI (US); Nandita Bal, Somerville, MA (US); David Lipson, Ithaca, NY (US)

(73) Assignee: Geri-Safe, LTD, Ithaca, NY (US)

( * ) Notice: Subject to any disclaimer, the term of this patent is extended or adjusted under 35 U.S.C. 154(b) by 87 days.

(21) Appl. No.: 17/306,919

(22) Filed: May 3, 2021

Related U.S. Application Data

(62) Division of application No. 15/374,444, filed on Dec. 9, 2016, now Pat. No. 10,993,881.

(60) Provisional application No. 62/266,114, filed on Dec. 11, 2015.

(51) Int. Cl.
*A61J 7/00* (2006.01)
*G16H 20/13* (2018.01)
*B25J 15/06* (2006.01)

(52) U.S. Cl.
CPC ......... *A61J 7/0084* (2013.01); *B25J 15/0683* (2013.01); *G16H 20/13* (2018.01); *A61J 2200/74* (2013.01); *A61J 2205/30* (2013.01)

(58) Field of Classification Search
CPC ............... G07F 17/0092; A61J 2205/30; A61J 2200/74; A61J 7/0084; B25J 15/0683; G06F 19/3456; G16H 20/13
See application file for complete search history.

(56) References Cited

U.S. PATENT DOCUMENTS

| | | | |
|---|---|---|---|
| 25,199 A | 8/1859 | Hoe | |
| 4,018,358 A | 4/1977 | Johnson et al. | |
| 4,697,721 A | 10/1987 | Johnson et al. | |
| 5,405,048 A | 4/1995 | Rogers et al. | |
| 5,480,062 A | 1/1996 | Rogers et al. | |
| 6,607,094 B2 | 8/2003 | MacDonald | |
| 6,997,341 B2 | 2/2006 | Pearson et al. | |
| 7,048,141 B2 * | 5/2006 | Abdulhay | G07F 11/10 221/3 |
| 7,080,755 B2 | 7/2006 | Handfield et al. | |
| 7,502,664 B2 | 3/2009 | Berg | |
| 7,587,259 B2 | 9/2009 | Berg | |
| 8,032,252 B2 | 10/2011 | Berg | |
| 8,060,246 B2 | 11/2011 | Berg | |
| 9,579,264 B1 * | 2/2017 | Litton | A61J 7/0481 |
| 10,993,881 B1 * | 5/2021 | Karpman | B25J 15/0616 |
| 2009/0112360 A1 | 4/2009 | Berg | |
| 2014/0025199 A1 * | 1/2014 | Berg | G07F 17/0092 700/232 |
| 2016/0042151 A1 * | 2/2016 | Akdogan | B25J 13/08 700/240 |

* cited by examiner

*Primary Examiner* — Timothy R Waggoner

(57) ABSTRACT

Disclosed is an invention for dispensing multiple medications to a patient over an extended period of days up to several times a day. The system includes a carousel with storage bins and a delivery bin on its periphery. A vacuum system and a vacuum probe with a vacuum cup at the end of the probe for grasping and holding by an induced vacuum a dosage of medication located in a storage bin and moving it to a dispending or delivery bin. The system includes a programmable computer to control the system and sequence the proper dispensing of the medication at the predesignated times.

3 Claims, 25 Drawing Sheets

APPARATUS AND METHOD FOR DISPENSING MEDICATION

CROSS-REFERENCE TO RELATED APPLICATIONS

This application claims the benefit of priority under 35 U.S.C. § 120 of: U.S. and any other relevant law of Provisional Application Ser. No. 62/266,114 filed on Dec. 11, 2015 and U.S. patent application Ser. No. 15/374,444 filed on Dec. 9, 2016 for "An Apparatus and Method for Dispensing Medication" the content of both of which is relied upon and incorporated herein by reference in its entirety.

TECHNICAL FIELD

The disclosure relates generally to an apparatus and method for dispending medication to a patient. More particularly it relates to a system and method for use by an individual that needs to take multiple medications to assure timely and accurate consumption of the prescribed medication.

BACKGROUND

Medications, in the form of pills, capsules, lozenges, tablets, bolus or similar form are taken by tens of millions of people around the world. Often the patient is taking a significant number of medications several times a day. Elderly patients make up a large portion of those taking multiple medications several times a day. These elderly patients tend to have limited cognitive abilities and physical impairments so assuring they are taking their medication at the right time and in the right dosages is a significant problem. Recent research articles published in Drugs and Aging Magazine state that a quarter of nursing home admissions resulted from problems with managing medications at home.

Automated medication dispensing systems have been one of the attempts to solve the problem of dispensing multiple medications. U.S. Pat. No. 6,607,094 describes one such attempt that uses a vacuum system with a probe to pick up pills from storage compartments located on a carousel and deposit the pills in chutes located next to the storage compartment, each compartment having a chute next to it. The need for the chutes adds undue structure and expense. Additionally, while this patent boasts a specially designed vacuum probe to pick up pills it in fact appears to be limited in utility and ability to grip pills for sufficient periods of time, thus requiring the chutes immediately adjacent to the storage compartment to drop the pills in to move them to a dispensing location.

Thus, it is an object of the present invention to provide a simple and easily manufactured apparatus to dispense pills and similar medications. It is a further object to provide a system with a vacuum based probe that can pick up and firmly grip and carry a large variety of medications. It is a further object to make it simple to load medications directly into the system. It is another object of the present invention to provide a system that efficiently and without mishap transfers medications for storage bins to a dispensing or delivery bin. It is a further object of the present invention to provide a system that can store up to a month's worth of at least 15 different medications. It is a further object to provide a device that can be programmed to dispense multiple medications on a regular basis several times a day if necessary. It is a further object to provide a system that once it is programmed the user will no longer need to worry about remembering when to take his or her medication and whether or not he or she has taken the medication.

No admission is made that any reference cited herein constitutes prior art. Applicant expressly reserves the right to challenge the accuracy and pertinence of any cited documents.

SUMMARY

The invention accomplishes these and other objectives by providing an apparatus for marshalling and dispensing multiple medications in a systematic and predetermined manner for consumption by a patient having; 1) a carousel with a plurality of bins on its periphery, wherein one of the bins a dispending bin dispenses medication and the remaining bins are storage bins for specified medications; 2) a robotic arm capable of being positioned for extraction of dosages of medication from the storage bins and depositing the extracted medications into the dispensing bin; 3) wherein the robotic arm has a vacuum probe with a distal end connected to a vacuum inducing system and a proximal end of the vacuum probe connected to a vacuum cup with an articulated body enclosing an interior chamber and an aperture at a center of a vacuum end of the vacuum cup that leads into the interior chamber, wherein the interior chamber is in fluid communication through an interior passage of the probe with the vacuum inducing system, c) wherein when the vacuum end of the vacuum cup is positioned by the probe to engage a surface of a dosage of medication upon initiation of the vacuum inducing system the vacuum end of the vacuum cup firmly holds the dosage of medication while the robotic arm moves it to the dispensing bin; and d) a computer controller system in which is registered the specific medication stored in a specific identified storage bin, and wherein in the controller system controls operation of the robotic arm to thereby direct the arm to extract dosages of medications from specified storage bins and deposit the dosages of medication in the dispensing bin at a preset time.

In a further aspect of the invention the storage bins are shaped to present a dosage of medication therein to the robotic arm such that the vacuum cup on the probe attached to the robotic arm can engage at a predesignated location in the bin a dosage of medication in the bin as the bin is emptied of dosages of medication. In yet another aspect of the invention the storage bins are shaped such that they have a large upper storage area and a lower funnel shaped area, the lower funnel shaped narrowing down to a termination point to which dosages of medication deposited in the bin will gravitate as other dosages of medication in the bin are removed.

In yet another aspect of the invention the articulated body enclosing the interior chamber of the vacuum cup is a bellows portion adjacent to the vacuum end and the vacuum end is a wide flexible surface surrounding the aperture.

In yet another aspect of the invention the computer determines if the vacuum cup has engaged a dosage of medication and is firmly holding upon receipt of a signal of an event selected from a group of events consisting of: a change in air pressure, a change in air flow, a change in force, and a change in weight.

In a further aspect of the invention its includes a device to scan a printed statement of prescription information of a medication being stored in a specific storage bin into the computer controller system, and software, including optical character recognition software, in the computer controller system to translate the prescription information on the printed statement into a form usable by the computer controller system to determine when to dispense the medication identified in the prescription information. In a further aspect the printed statement of the prescription can be scanned from the label on a prescription container, and or a sheet with the prescribing information that is provided by the pharmacist on dispensing the prescription.

In another variation of the invention it provides a system for dispensing multiple medications in the form of solid dosages to an individual having: 1) a programmable computer for controlling an operation of the system; 2) a carousel rotatable about its center point with multiple storage bins on a periphery and at least one delivery bin on it periphery; 3) a robotic arm with a vacuum probe, wherein the robotic arm is configured to move about the bins and insert the vacuum probe into any one of the multiple storage bins and at least one delivery bin as instructed by the computer; 4) a vacuum generating apparatus attached to a first end of the probe; 5) a vacuum cup, with an articulated body surrounding an interior space, attached to a second end of the probe, wherein the vacuum generating apparatus, the interior space of the vacuum cup are in fluid communication through the probe which has a hollow interior forming a fluid connection there between; 6) the vacuum cup having a broad pliable pill contacting surface surrounding an orifice leading into the interior space of the cup; and 7) wherein when the second end of the probe is inserted into anyone of the multiple storage bins and the pill contacting surface of the vacuum cup makes contact with a dosage of medication and the vacuum generating apparatus is functioning the vacuum cup grasps and securely grips the dosage of medication and continues to grip it until the robotic arm moves it to a position above the delivery bin where the computer system terminates the grip by the cup on the dosage of medication causing the dosage to fall into the delivery bin.

In a further aspect of the invention the computer terminates the grip of the vacuum cup on the dosage of medication by terminating operation of the vacuum inducing apparatus. In another variation the computer terminates the grip of the vacuum cup on the dosage of medication by reversing fluid flow between the vacuum cup and the vacuum inducing apparatus. In yet another aspect of the invention reversing air flow is used to clear the system of any particulate matter that may be in the vacuum system from the dosages of medication that vacuum cup has picked up.

In yet another aspect of the invention the computer determines if the vacuum cup is securely holding a dosage of medication by receipt of a signal of an event, the event selected from a group consisting of: a change in air pressure, a change in air flow, a change in force, and a change in weight. In yet another aspect of the invention the articulated body of the vacuum cup is a bellows section located adjacent to the broad pliable pill contacting surface of the vacuum cup.

Additional features and advantages will be set forth in the detailed description which follows, and in part will be readily apparent to those skilled in the art from the description or recognized by practicing the embodiments as described in the written description and claims hereof, as well as the appended drawings.

It is to be understood that both the foregoing general description and the following detailed description are merely exemplary, and are intended to provide an overview or framework to understand the nature and character of the claims.

The accompanying drawings are included to provide a further understanding, and are incorporated in and constitute a part of this specification. The drawings illustrate one or more embodiment(s), and together with the description serve to explain principles and operation of the various embodiments.

DETAILED DESCRIPTION

Overview of the System

In this disclosure the reference to "medications" will be used as a reference to medicines that can be dispensed in preset and premade dosages such as pills, tablets, gels, lozenges, boluses, gels or similar forms.

Figure 1:
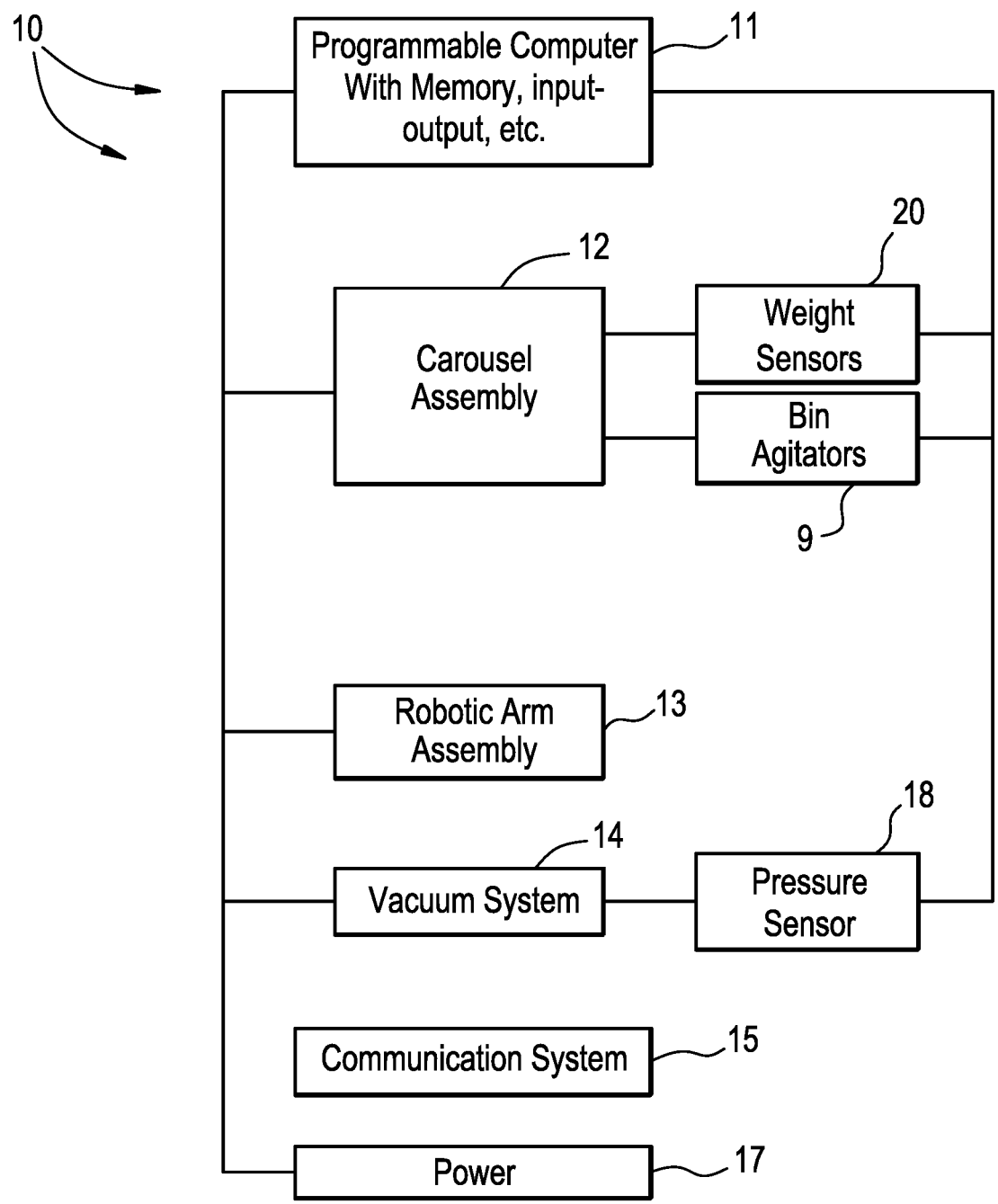
FIG. 1 is a block diagram of the major functional subsystems of one embodiment of the present invention.

FIG. 1 is a block diagram of the major parts of an embodiment of the subject invention 10. A programmable computer 11 controls the operation of the system. The system includes a carousel assembly with storage bins and a dispensing bin 12, a robotic arm assembly 13, which includes a vacuum or suction cup that pickups medication in a storage bin and moves the medication to the dispensing bin, and a vacuum system 14 that creates the vacuum to thereby enable the vacuum cup to grasp medication in the storage bins and move it to the dispensing bin. A pressure sensor and/or air flow sensor 18 to determine if and when the vacuum cup has griped a dosage of medication. Weight sensors 20 to verify the contents of the storage bins and the dispensing bins, among other things. The system also includes bin agitators 9 to shake the bins if for some reason the medications become logged in the bin and do not move. The system includes a communication capability 15 and power supply 17.

Programmable computer 11 is a standard programmable computer designed to work with and control the system. It includes memory, input output capability, and the other standard capabilities of a programmable computer that are well know in the art. It will be programmed to among other things to receive information regarding medications loaded into its storage bins, and control and sequence the functions of the system including the dispensing of medications. The system will keep detailed information on the medication dispensed, time dispensed, amount dispensed, etc. This information will be kept in memory of the system and transferrable to a portable memory device. The information on the medications once transferred to the portable memory device can then be downloaded to the patients treating physicians' computer medical records so the physician has a complete and accurate record of the medications taken and the time they were taken and quantity taken.

Communication system 15 enables computer 11 to send messages to the patient and patient's care giver that it is time for the patient to take his or her medications. The system will have the capability of sending such messages over a wifi system, blue tooth system, the commutation system of a common carrier such as ATT or Version or a combination of such systems. The message can thus be sent to a computer or mobile communications device like a cell phone. The system can also be programmed to transmit the information on medications dispensed to the patient's physician's computer system over a secure link via the communication capabilities of the system.

Carousel and Robotic Arm Assemblies

Figure 2:
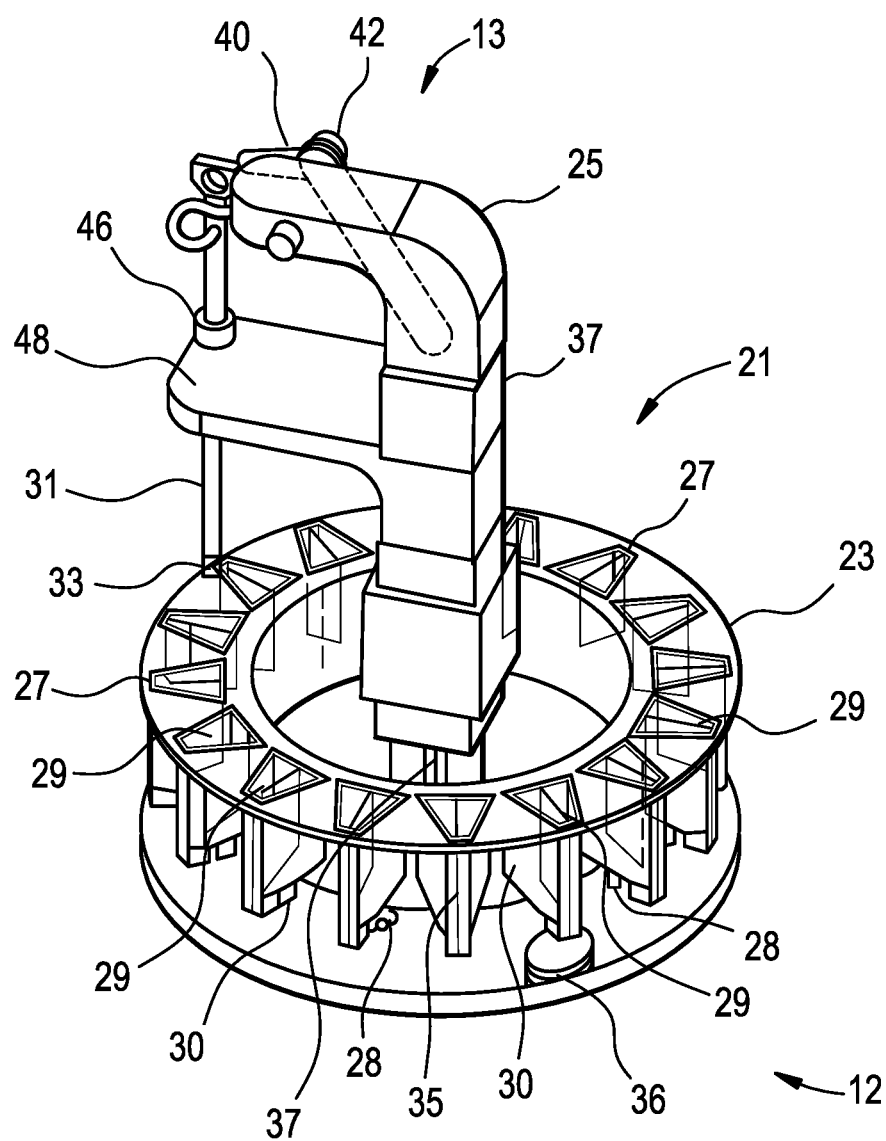
FIG. 2 is a raised perspective view of an embodiment of the of the robotic arm assembly and carrousel assembly of the present invention.

FIG. 2 is a raised perspective view of carrousel assembly 12 and robotic arm assembly 13 of the medication dispensing apparatus of the subject invention. These include a carousel 23 and robotic arm 25. Around the periphery of the carousel are disposed a dispensing bin 29 and multiple storage bins 27 In FIG. 2, there are fifteen storage bins 27 for storing up to fifteen different medications and only one dispensing bin 29. In this embodiment, the external shape of the bins have been optimized to fit 16 bins on the carousel, for storage of medications and one for dispensing medications. Each storage bin will contain a specific medication arbitrarily set by the user. Each bin has a weight sensor 20 to verify whether the storage bins are full and the approximate amount of dosage left in each storage bin as the system dispenses medication. The dispensing bin also has a weight sensor that indicates whether there is medication in the bin or it has been dispensed. Also, each of the bins 27 have their own agitators 30 to regularly shake the bin to assure the medications they hold do not get caught or stuck. In the embodiment shown carousel 23 has a diameter of inches and room as noted for sixteen bins around its periphery for a total of 15 storage bins 27 and one dispensing bin 29. However, the size of the carousel and the number of bins can be varied as desired without departing form the spirit of the invention.

Robotic arm 25 has a vacuum probe 31, which has positioned at its end vacuum cup 33. Vacuum probe elevation motor 37 is located in the upper portion of robotic arm 25. Vacuum probe elevation motor 37 in the embodiment shown provides the means for raising and lowering vacuum probe 31. Attached to the bottom of the robotic arm is robotic arm rotation motor 35. Below the robotic arm rotation motor is carousel rotation motor 39.

Figure 3:
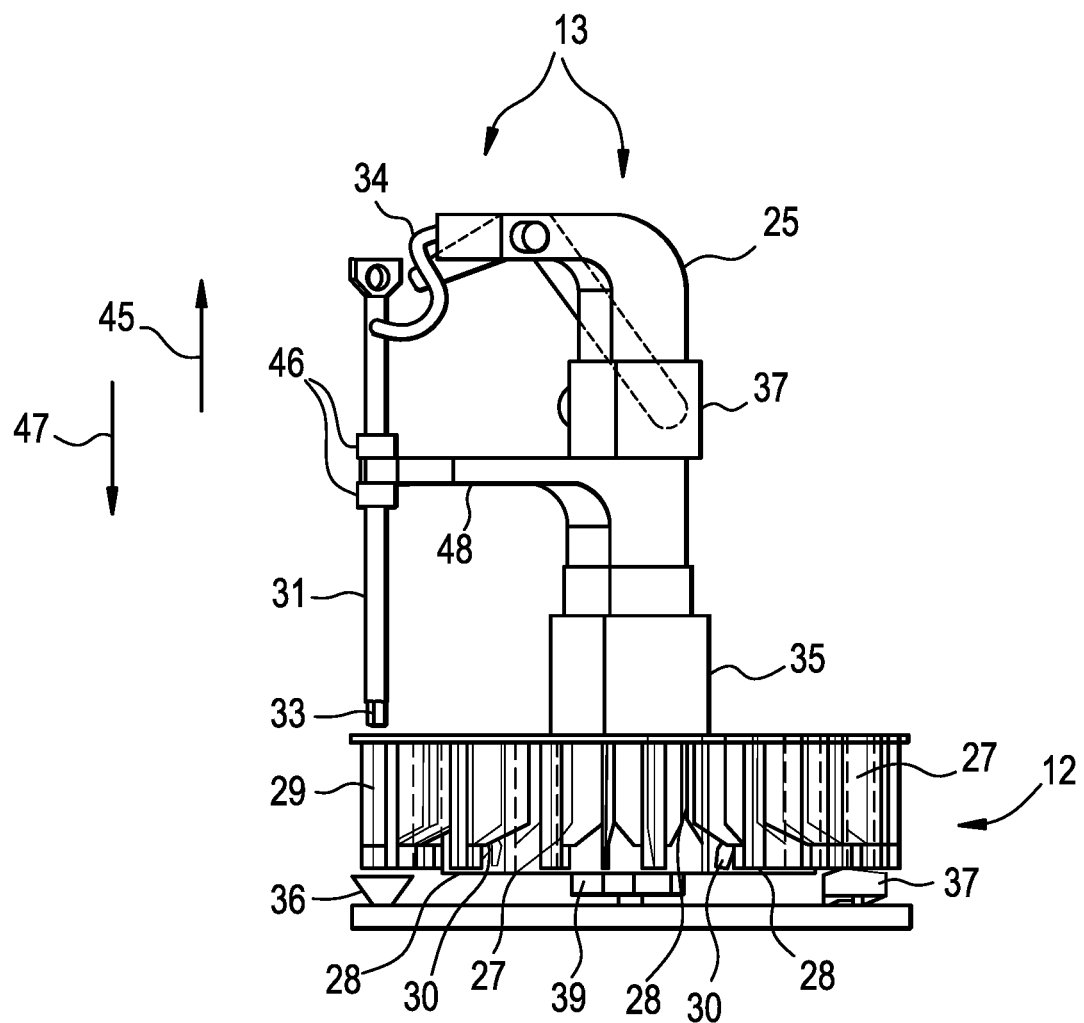
FIG. 3 is a side view of the embodiment depicted in FIG. 2.

FIG. 3 is a raised plain view of carrousel assembly 12 and robotic arm assembly 13 in which robotic arm rotation motor 35 has moved robotic arm 25 to position at which vacuum probe 31 with vacuum cup 33 are above dispensing bin 29 with medication dispensing cup 36 situated below the dispensing bin. Vacuum probe 31 extends through sleeve 46 at the edge of strut 48 on the robotic arm. Vacuum probe 31 is free to slide up-arrow 45 and down-arrow 47 thorough sleeve 46. Sleeve 46 keeps vacuum probe 31 constrained to linear movement in the vertical direction. Also, visible is carousel 23 rotation motor 39. Rotation motor 39 is controlled by the computer which moves the carousel around as needed.

FIG. 3 also provides a better view of flexible hose 34 that connects vacuum probe 31 to the rest of pneumatic vacuum system 49. Flexible hose 34 has sufficient slack to allow for the movement of vacuum probe 31 in an upward direction 45 and a downward direction 47 to allow vacuum cup 33 to be inserted into each of the bins to extract medication but then to moved up out of the bin so robotic arm 25 can rotate vacuum probe 31 around to the next selected bin. Vacuum probe 31 is hollow inside to allow for fluid flow, typically air or an inert gas, between the vacuum system and the vacuum cup.

Figure 4:
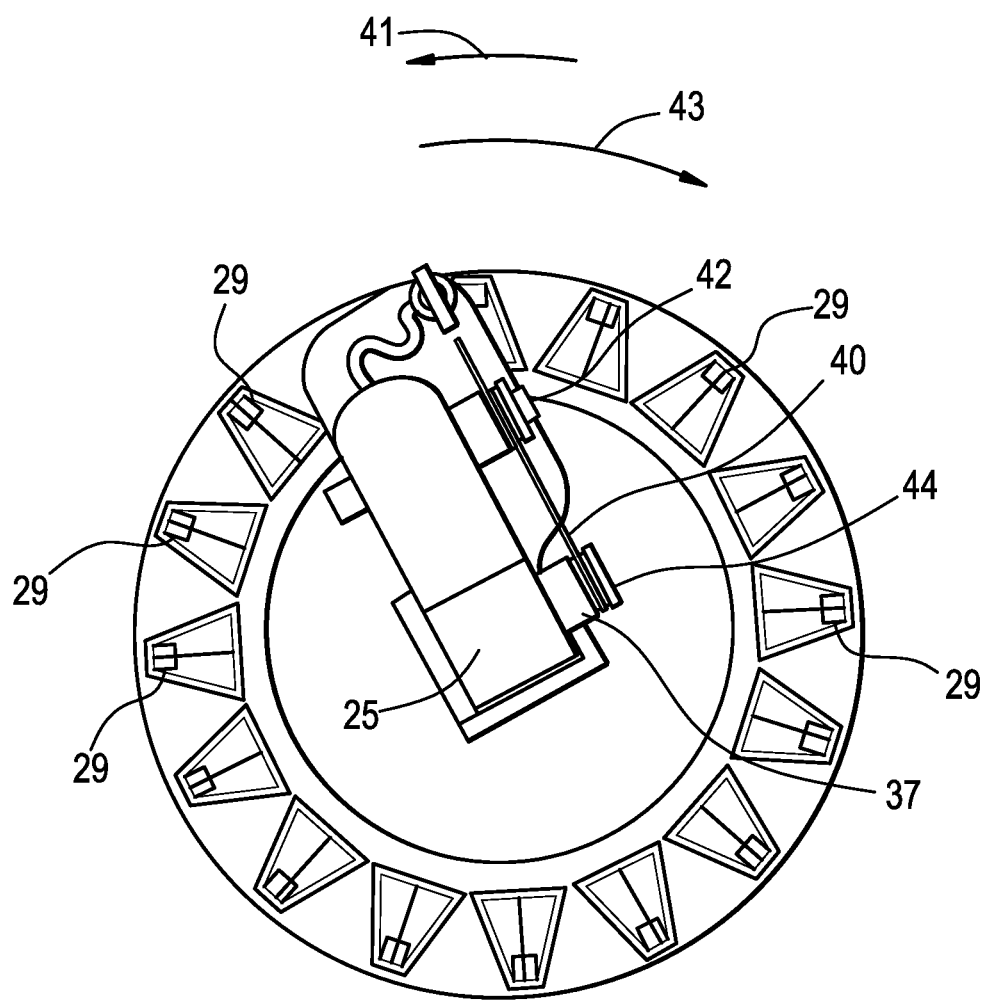
FIG. 4 is a top view of the embodiment depicted in FIG. 2.

FIG. 4 provides a top view of carrousel assembly 12 and robotic arm assembly 13. Cable 40 at one end attached to the upper end of vacuum probe 31 and at its opposite end cable 40 attaches to pulley 42. Cable 40 winds off pulley 42 as pulley 42 is turned in a clockwise direction and winds onto pulley 42 when it is turned in a counter clockwise direction. Drive belt 28 dynamically connects pulley 42 and drive shaft 44. Drive shaft 44 is driven by motor 37. Thus when drive shaft 44 is moved in a clockwise direction by motor 37 belt 28 movement and causes pulley 42 to move in a clockwise direction and cable 40 to spool onto pulley 42. This in turn causes probe 31 to move up 45 FIG. 3. When drive shaft 44 is moved in a counter clockwise direction by motor 37 belt 28 turns pulley in a counter clockwise direction which causes cable 40 to spool off of pulley 42 which in turn causes vacuum probe 31 to move down 47 FIG. 3.

The embodiment of the robotic arm described herein is one example used for illustrative purposes. It is a very simple design with limited degrees of motion, namely rotary motion of robotic arm 25 provided by motor 35. Translational motion of vacuum probe 31 up 45 and down 47 is provided by motor 37, pulley 42 and cable 40 attached to the end of vacuum probe 31. The computer controls robotic arm 25 and thus operation of motors 35 and 37 and thus can positions vacuum probe 31 over the selected storage bin or the dispensing bin by rotating arm 25 into position with motor 35 and then lower and raise vacuum probe 31 with motor 37 to extract the medication from a storage bin and deliver it to the dispensing bin. Hose 34 has enough slack to allow for movement of vacuum probe 31 up and down while maintaining the integrity of the seal of the vacuum system. Those of ordinary skill in the art of robotics will readily appreciate that there are a multitude ways to configure a robotic arm for the necessary movements to achieve the results described herein. There is a significant amount of robotic art that allows longitudinal or liner motion, translation motion and rotary motion. Such systems can be hydraulic, or gear driven. All such schemes have been well described in the prior art and can be developed and adapted for the present invention.

As noted a computer appropriately programmed controls the system. In operation, each storage bin 27 is filled with a specific medication prescribed for the patient that is using the medical dispensing system of the present invention. In the version shown in FIGS. 2, 3 and 4, this as noted is for up to 15 different medications. The process of filling each bin and recording its contents in the computer will be discussed below. Once each bin is filled with a specific medication, not shown, the system is programmed for dispensing the medication. The marshalling of the medication occurs as follows, referring to FIG. 4, robotic rotation motor 35 rotates robotic arm 25 either a clockwise 43 or counterclockwise 41 direction to place vacuum probe 31 over a preselected storage bin 27 of the specific medication to be dispensed.

Referring to FIG. 2, robotic arms upon activation of elevation motor 37 moves vacuum probe 31 downward 47 to allow vacuum cup 33 to engage one dosage of the medication located in the particular storage bin 27 selected. When vacuum cup 33 establishes positive contact with a dosage of medication the vacuum system, which has been activated, creates a vacuum or suction effect that causes the vacuum cup to firmly grip the dosage of medication. Once the seal is established, vacuum probe 31 is raised up 45 so that vacuum cup 33 with the medication attached are clear of storage bin 27. Additionally to prevent medication stored in each bin 27 form jamming or getting stuck each bin has an agitator to shake it to dislodge any medication that may have become stuck.

Referring to FIG. 3, robotic arm 25 then rotates in either a clockwise 43 or counter clockwise 41 direction until vacuum probe 31, vacuum cup 33, and the medication held by the vacuum cup are positioned above dispensing or delivery bin 29. At this point the dosage of medication held by vacuum cup 33 is released and falls into the dispensing bin 29. Release of the dosage of medication is typically triggered by the computer signaling the vacuum system to cease creating the vacuum causing the dosage of medication to fall into the dispensing bin. In another variation the system could switch from a negative air pressure to positive air pressure thus forcing or pushing the medication into bin 29. Robotic arm 25 moves successively to each storage bin 27 that has a particular medication to be dispensed to the patient at the preset time, picking it up with the vacuum cup 33 and then depositing the medication into the dispensing bin 29. It does this in successive steps until all of the medication that the patient has been scheduled to take at a preset time is in dispensing bin 29.

Vacuum System

Figure 5:
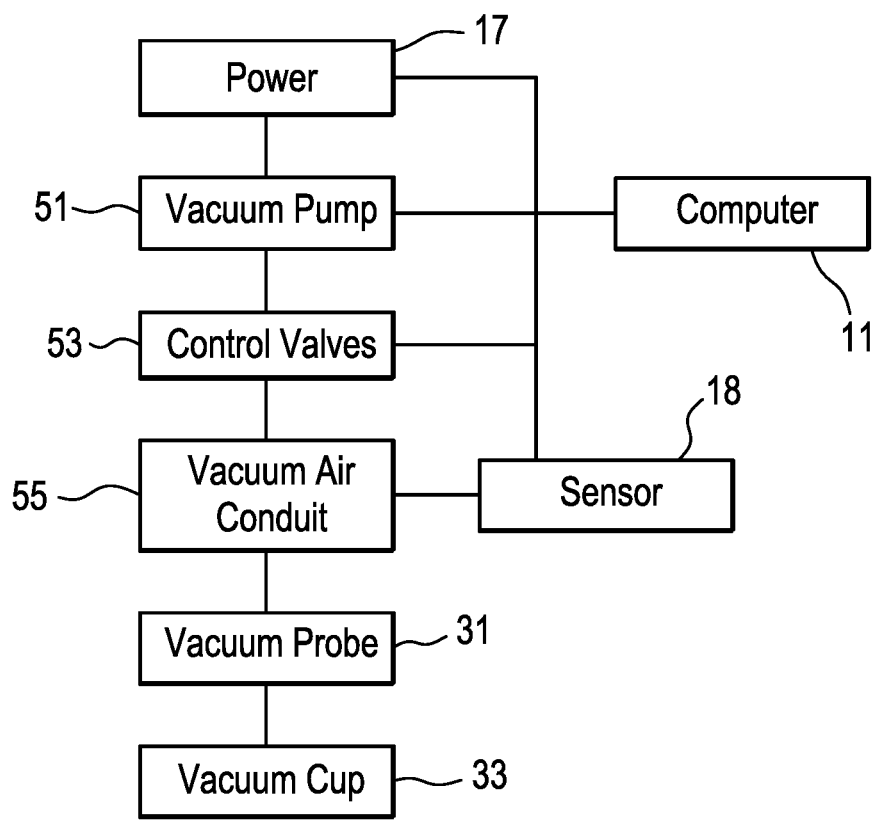
FIG. 5 is a block diagram of the components of an embodiment of a pneumatic vacuum system.

FIG. 5 is a block diagram of the basic parts of vacuum system 49 used to move dosages of medications from the storage bins to the dispensing bin. The basic parts are the vacuum pump 51, vacuum cup 33, control valves 53, air tight vacuum conduit 55 connecting the vacuum pump 51 through vacuum probe 31 to vacuum cup 33, and pressure and/or air flow sensor 18. Power supply 17 energies the system and computer 11 controls operation.

Figure 9:
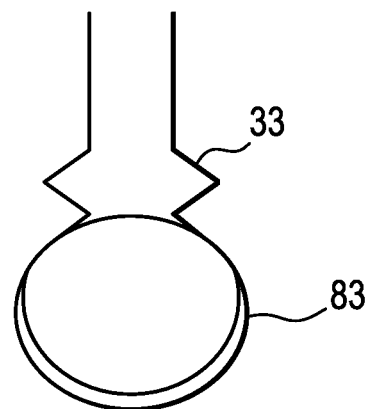
FIG. 9 depicts examples of the vacuum cup of the present invention picking up medications of varying shape and size.
Figure 9:
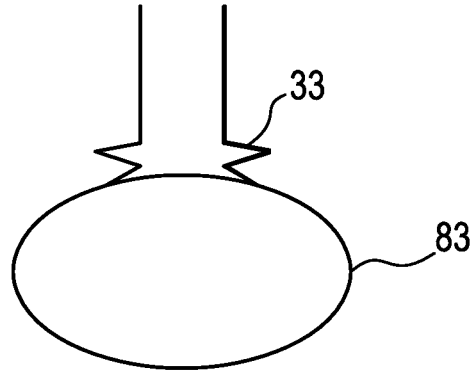
Figure 9:
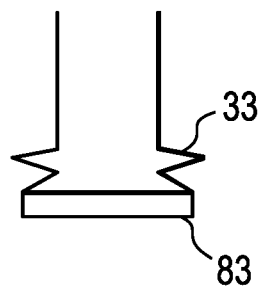

As noted above computer 11 positions robotic arm with vacuum probe 31 and vacuum cup 33 above a preselected storage bin at which point it lowers vacuum probe 31 down until the vacuum cup engages a dosage of medication stored in the bin and makes positive contact and successful pickup of a dosage of medication 83 in a storage bin. FIG. 9 provides examples of cup 33 engaging and grasping medications 83 of varying shapes and sizes. In the embodiment shown the vacuum system is continuously running and when vacuum cup attaches to a dosage of medication a sudden change or decrease in air pressure, or a drop in air flow detected by the pressure and/or air flow sensor 57 indicates a pill is attached to the vacuum cup for pickup.

In the embodiment shown the vacuum pump is located in robotic arm 25 and connects to vacuum cup 33 by vacuum air conduit 55, FIG. 5. However, in an alternative embodiment the vacuum motor could be located adjacent to vacuum cup 33 at the end of probe 31. In such an alternative embodiment, a miniature motor and vacuum pump can be combined into the structure of the vacuum cup.

In another embodiment a force gauge or weight sensor could be used to determine when vacuum cup 33 has engaged a dosage of medication. In such a system once positive contact has been made computer 11 would then activate vacuum pump 51 and control valves 53 to create a vacuum at or below atmospheric pressure in air conduit 55 and cause suction cup 33 to engage and pick up and hold a dosage of medication in a vacuum induced grip.

Pneumatic systems that generate air flow are well known in the art. At one time banks and stores use them to move shuttles with cash or other documents around the store or bank and in fact are used to day in drive up teller facilities to move cash and other documents between the teller in the bank and the customer seated in his or her car. Thus, systems that can reverse air flow are well known in the art. One of the aspects of the present invention is that it can reverse air flow for a number of reasons. One being a cleaning or purging cycle where the pneumatic vacuum system clears or purges particulate matter that may have infiltrated the system from the dosages of medication stored in and moved around by the pneumatic vacuum system. Additionally, the pneumatic system of the present invention also could be used to rotate the carousel or move the robotic arm and probe around, thus creating pneumatic drive system.

Vacuum Cup Assembly

Figure 6:
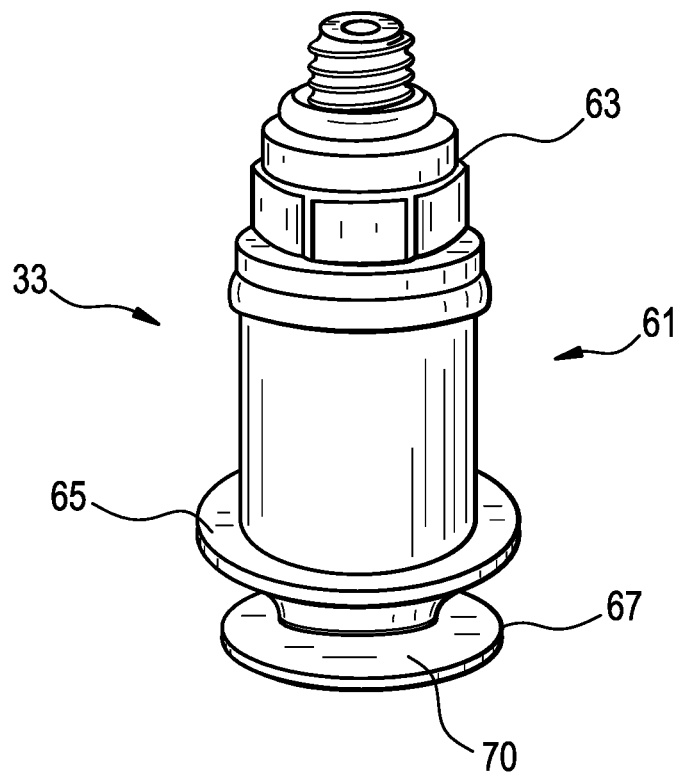
FIG. 6 is a perspective view of an embodiment of a vacuum cup for pickup of medication.

FIG. 6 provides a perspective view of the vacuum cup 33 which has a body 61 made of a pliable material. In the embodiment depicted the vacuum cup is made of silicon; however, any suitable similar material can be used. Attached at one end of the body 61 is metal connector 63 that has threads 64 to connect vacuum cup 33 to vacuum probe 31 which in turn in the embodiment shown connects to the rest of vacuum system 49 through hose 34 and vacuum air conduit 55. The vacuum end 67 of the vacuum cup is at the end of body 61 opposite metal connector 63. Body 61 of the vacuum cup 33 is articulated, which in this embodiment takes the form of a bellows configuration 65, which increases the flexibility and pliability of cup 33 and thus its ability to securely fit surface 68 against a dosage of medication to create a secure air seal.

Figure 7:
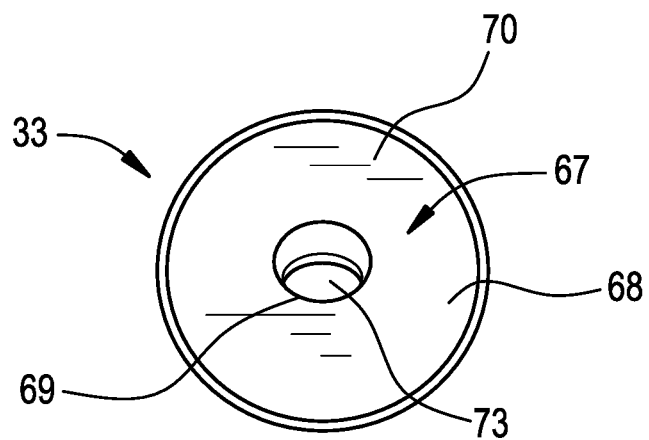
FIG. 7 is a bottom view of the proximal pill contacting surface and pill contacting orifice located at its center, of the embodiment of the vacuum cup depicted in FIG. 6.
Figure 8:
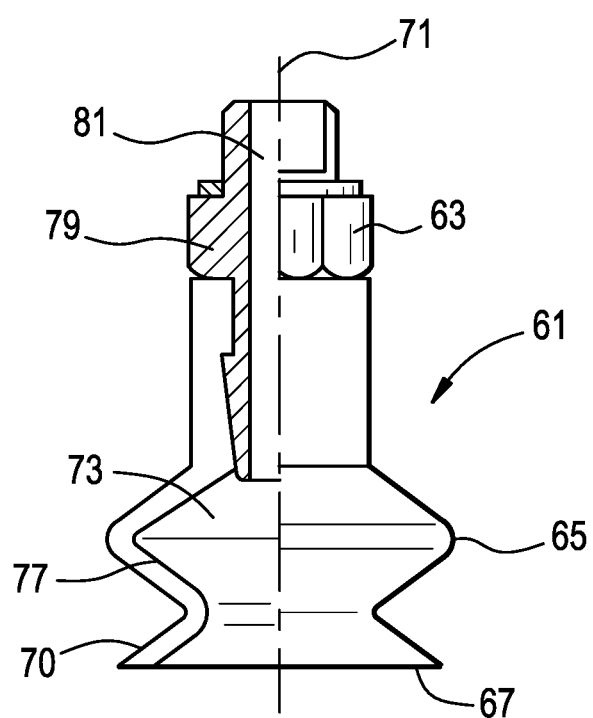
FIG. 8 is a partial cut away view of the embodiment of the vacuum cup depicted in FIG. 6.

FIG. 7 provides a view of the vacuum end 67 with pill contacting surface 68 with pill contacting orifice 69 of vacuum cup 33. Aperture or orifice 69 is in the center of pill contacting surface 68. Orifice 69 opens into the hollow interior 73 of vacuum cup 33. FIG. 8 is a plain view of vacuum cup 33 with a partial cut away view along line 71 to show hollow interior 73 on the left side of line 71 as opposed to the exterior on the right side. The interior surface 77 of vacuum cup body 61 is viewable. As can be seen connector 63 extends down into the interior of vacuum cup body 61, a cross sectional view of a portion 79 of connector 63 is shown. Also, air passage 81 extends up the interior of connector 63 to allow for air flow from the interior of vacuum cup body 61 to the vacuum probe and then to the vacuum air conduit not shown in FIG. 8.

Thus, vacuum cup 33 is designed to create an air tight seal with a dosage of medication and pick it up and move it from the preselected storage bin to the dispensing bin. It does it because of the soft pliable material that the body 61 of the vacuum cup is made up of and the vacuum end 67, which because of its soft pliable nature can conform to the shape of medication it is pushed against. As depicted in FIG. 9 medications 83 come in a variety of forms, capsules, pills, lozenges, tablets, boluses, etc. Additionally, the size, shape and weight vary significantly. As depicted in FIG. 9 vacuum cup 33 is illustrated picking up spherical shaped, egg or ellipsoid shaped and flat shaped dosages of medication. As can be seen vacuum end 67 of vacuum cup 33 has easily wrapped its contacting surface 68 around each of the dosages of medication 83 and securely holds it by the vacuum suction created at orifice 69. FIG. 9 is only for illustrative purposes; in actual operation each bin will hold only one specific medication as discussed in detail elsewhere. Bellows 65 of vacuum cup body 61 provides extra flexibility that allows vacuum cup vacuum end 67 to form a complete seal and thus hold the pill and move it without dropping it. Bellows 65 portion adds articulation to the body of vacuum cup 33 to thereby provide greater flexibility.

As depicted in FIGS. 5, 6, 7 and 8 vacuum or suction end 67 is formed by a large lip like structure that extends out like a disk shaped flange 70 forming the pill contacting surface 68 around aperture 69. As noted the material the suction or vacuum cup is made of is a soft pliable rubber or silicon material. Many such materials exist such as nitrile, neoprene, polyurethane, silicone, natural or artificial rubber, etc.

Figure 8A:
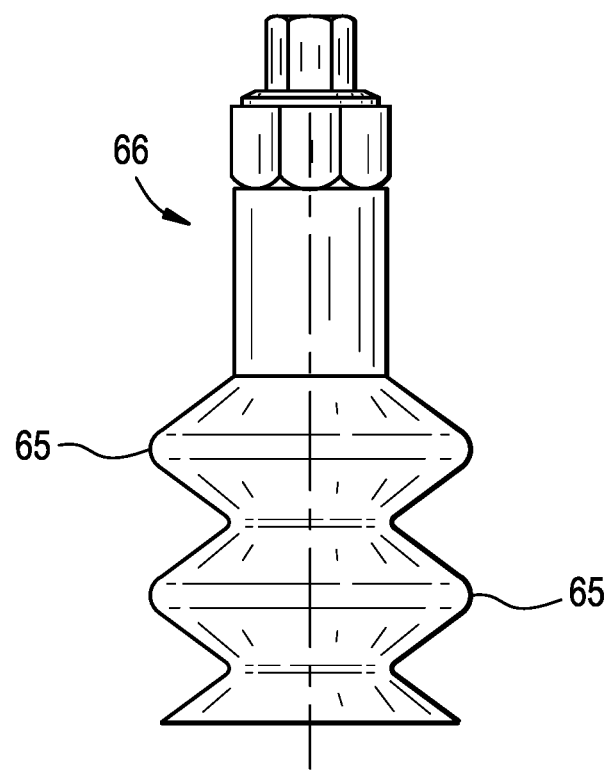
FIG. 8A a double bellows variation of the vacuum cup depicted in FIGS. 6, 7, and 8.

Although the embodiment of the cup depicted herein is round, the cup may also be shaped in a variety of shapes including elliptical or oblong and still be within the concept of the invention herein. FIG. 8A provides a side view of a vacuum cup 66 that has two bellows 65, which makes it a double bellows vacuum cup. Given the flexible material the cup is made of a flexible silicon or rubber like material, the double bellows provides even more flexibility to the vacuum cup allowing it to more easily grasp and hold medication of varying size, weight and shape. In fact in some instances a multiple bellows cup with more than even two bellows may have advantages.

The preferred embodiment uses a vacuum cup as depicted in FIGS. 6, 7 and 8 has an outside diameter around vacuum end 67 of at least 1.25 inches and an aperture 69 of no more than 0.25 inches. As noted computer 11 based on readings from pressure and/or air flow sensor 57 can determine if and when the vacuum cup has successfully created a seal with the dosage of medication and can thus can pick it up and move it. However, the forgoing dimensions can be varied without departing from the concept of the present invention.

Figure 10:
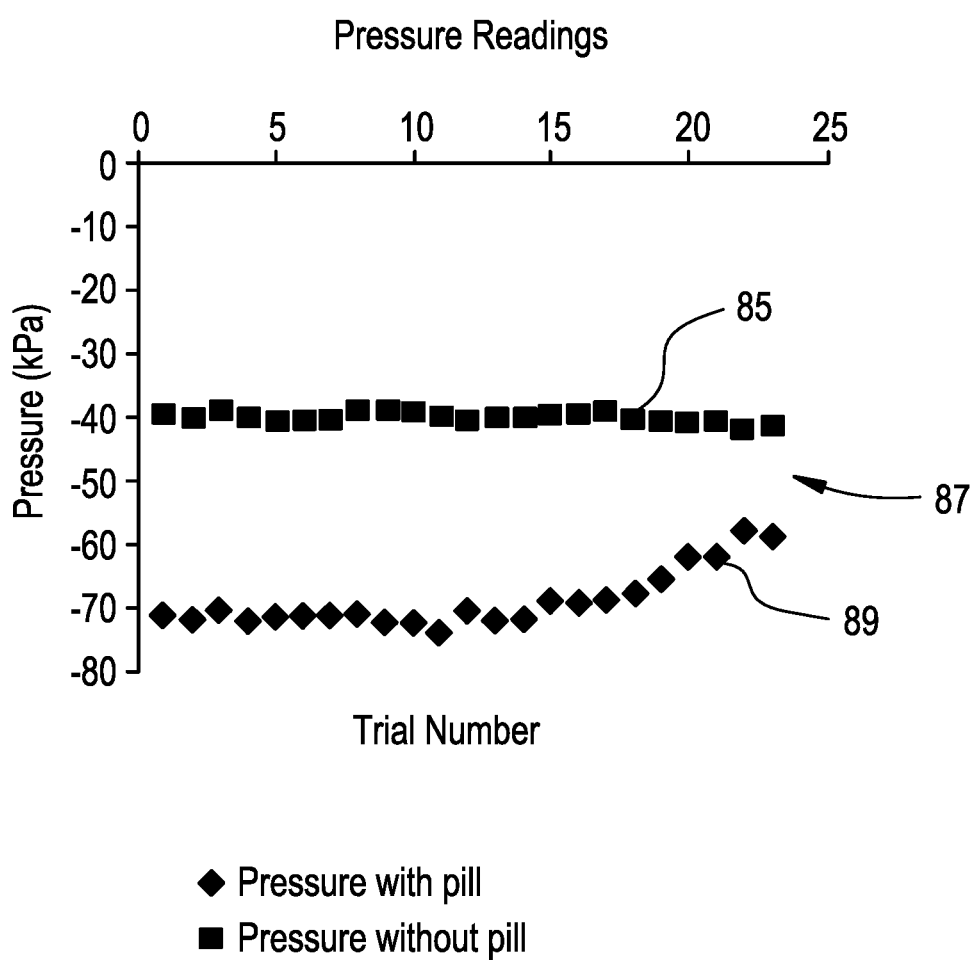
FIG. 10 is a graph depicting the pressure signature signal the computer receives on successful contact and pickup of a dosage of medication and the pressure signature signal that the computer receives when there has been a failure to picked up a dosage of medication.

In the embodiment of the invention discussed above it has been determined the system of the present invention has a threshold pressure of −50 kPa (kilopascals) when the vacuum cup has engaged and is holding a medication with a firm enough grip to transport it from the storage bin to the dispensing bin. Pressures will be less than the surrounding atmosphere. Air flow in the vacuum is sufficient when the vacuum is at least −25 kPa and air flow is at least 0.8 scfm (standard cubic feet per minute). FIG. 10 is a graph on which the vertical axis is the pressure scale and the horizontal axis are individual tests. Blocks 85 show the pressure signal the computer received in situations in which the vacuum cup did not securely gripe a dosage of medication, generally in the −40 kPa range. Diamonds 89 show the pressure signal the computer received when the suction cup had firmly gripped the dosage of medication, it being in the −58 to −75 kPa range. The threshold pressure 87 at which the cup is able to grasp a dosage was at or below −50 kPa as noted above. It is not shown on the graph but the pressure for the largest medications can go as high as −0.820476 kPa (−0.119 psi). While these are empirically derived pressure readings, alternative pressure ranges can be used depending on the CC/min flow rate in the pump, size of the vacuum tubing, and weight or shape of the pills.

Thus, the system of the present invention can handle the smallest medications, which for example can have a weight of 0.00012474 oz. (ounce) and a diameter of 0.25 inches. It can handle medium sized medications in the weight range of 0.0035046 oz. to 1.8631 oz. and diameters of 0.875 inches to 1 inch. It can also handle large medications of 2.6378 oz. and diameters of 0.75 inches.

Carousel Storage Bins, and Dispensing Bin

The embodiment of the present invention disclosed herein has 15 storage bins and one dispensing bin disposed around the periphery of the carrousel as described above. However, the number of storage bins can be varied without departing from the spirit of the invention. Unfilled storage bins will be ignored by the system. The primary design criteria of the storage bin is that it can store a sufficient supply of medication for at least a one month's dosages and present and concentrate the dosages of medication in the same position when the vacuum cup on the robotic is in the same location in the storage bin as the bin is gradually emptied during operation of the system over the course of the month or so. The design of the storage bin depicted in FIGS. 11A and 11D positions the dosages of medication in the center of the bin as the bin is emptied. On the other hand the embodiment of the storage bins depicted in FIGS. 12, 13A, 13B, 13C, and 13D, as will be discussed below, concentrates the dosages in a well adjacent to one of the walls of the bin as it is emptied. Thus, the slope or draft on the internal surface of a container can vary and still be configured to concentrate items located in a container at a specific location to facilitate pickup for dispensing.

Figure 11A:
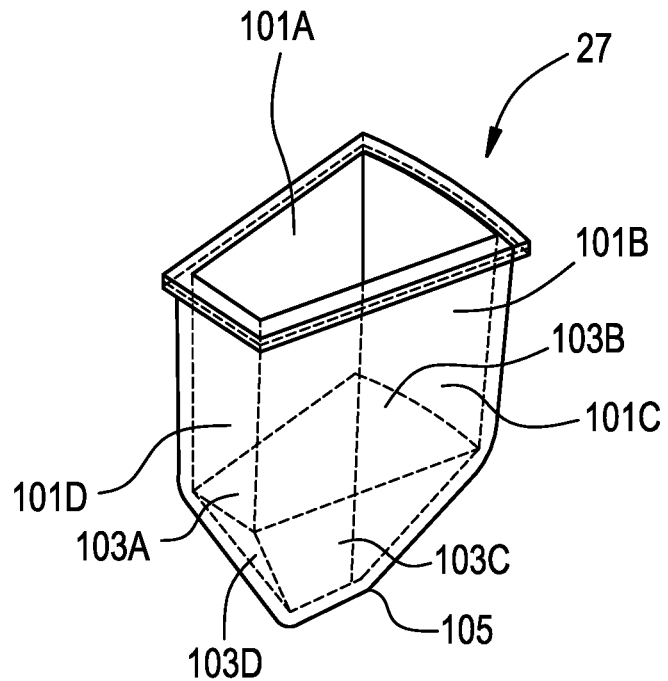
FIG. 11A is perspective view of an embodiment of a medication storage bin.

FIG. 11A is a perspective view of one embodiment of a storage bin 27. In FIG. 11A the interior surface of the bin is shown in dotted outline for the purposes of illustration. Bin 27 has four upper sides 101A, 101B, 101C and 101D which have only a slight inward slop down. This allows the bin to hold a significant number of pills or other similar type of medication. Sides 101A,101 B, 101C and 101D terminate at their bottom is steeper sloping walls 103A, 103B, 103C and 103D, which due to their steepness form a funnel that terminates in a closed v shaped bottom 105. The system also includes a shaker to shake the storage bins and or the carrousel to cause the medication to fall towards the bottom 105 if for some reason it was caught up or jammed in the bin.

Figure 11B:
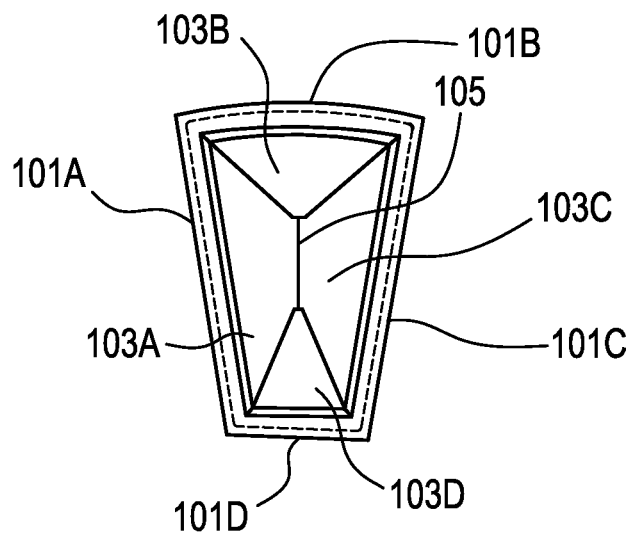
FIG. 11B is a top view of the embodiment of the medication storage bin of FIG. 11A.

FIG. 11B is a top view of storage bin 27 that shows the positon of the walls and bottom 105 which shows that the medication as it is removed will fall to the bottom 105 and positioned for extraction of by the robotic arm which positions the vacuum cup directly above bottom 105.

Figure 12:
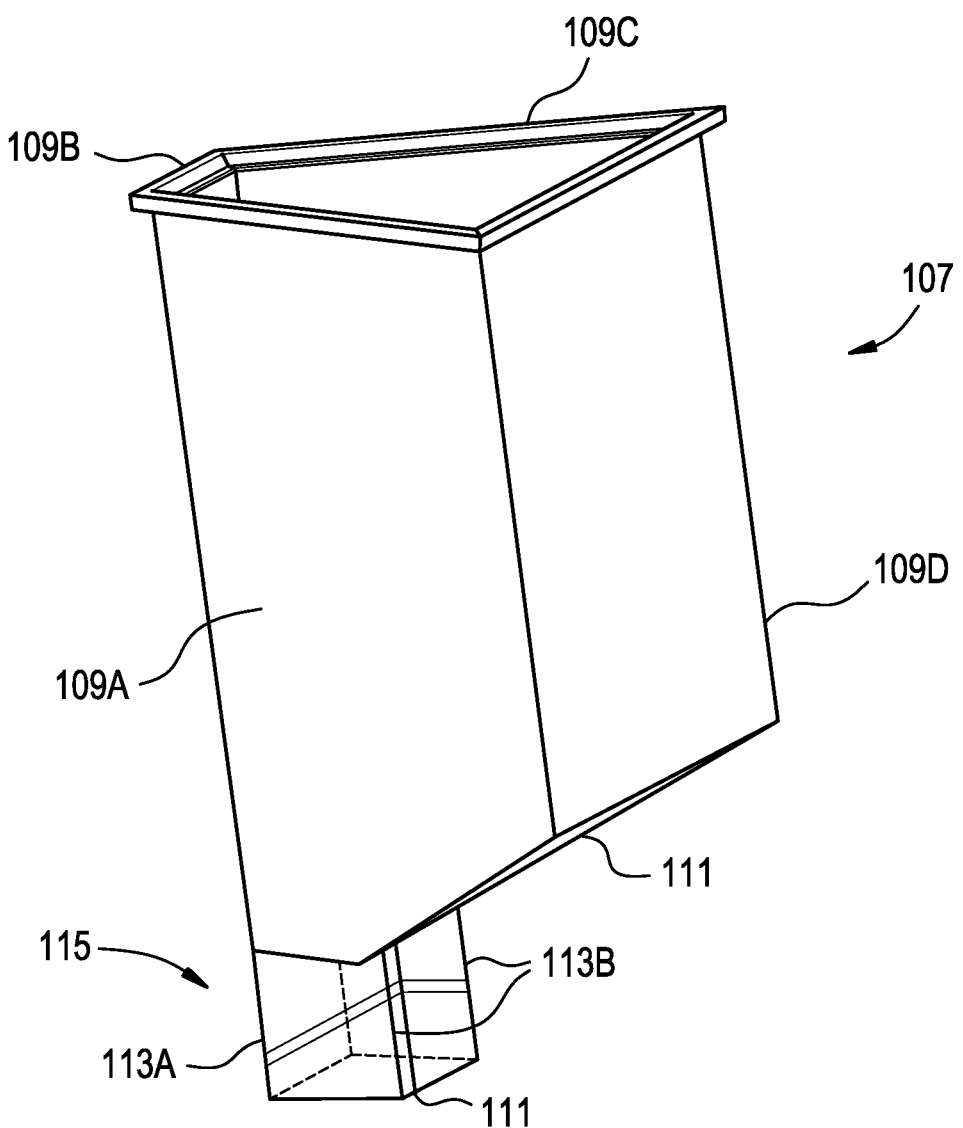
FIG. 12 is a perspective view of another embodiment of the storage bin, which can also be used as a dispensing bin.
Figure 13A:
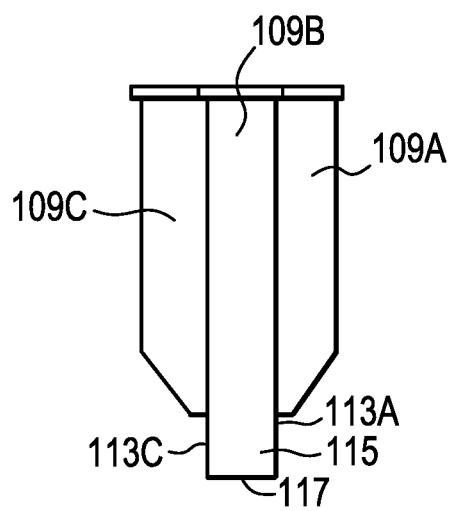
FIG. 13A is a front view of the storage bin depicted in FIG. 12.
Figure 13B:
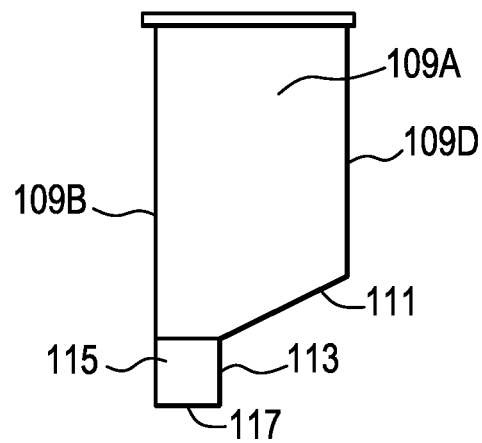
FIG. 13B is a side view of the storage bin depicted in FIG. 12.
Figure 13C:
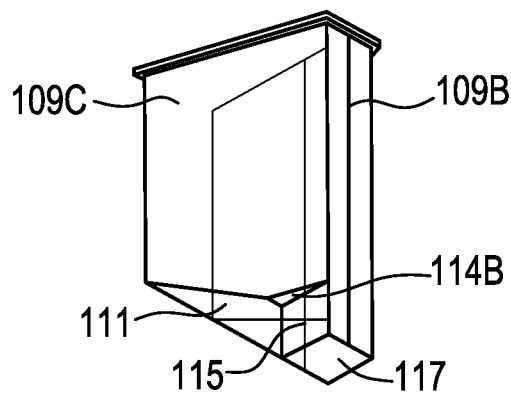
FIG. 13C is a side view of the storage bin depicted in FIG. 12.
Figure 13D:
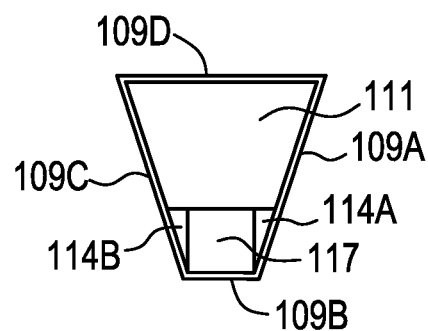
FIG. 13D is a top view of the storage bin depicted in FIG. 12.

FIG. 12 depicts another embodiment 107 of the storage bin. FIG. 13A is a front view of storage bin 107, FIG. 13B is a side view of storage bin 107, FIG. 13C is a perspective view looking up at storage bin 107 and FIG. 13D is a top view of storage bin 107.

As depicted in FIGS. 12, 13A, 13B, 13C and 13D embodiment 107 of the storage bin has four high sides, 109A, 109B, 109C, and 109D. Side 109B is the longest and extends all of the way to the bottom of storage bin 107. Side 109D, which is wider, terminates in sloping side 111. Sides 109A and 109C terminate on either side of sloping side 111 and at the beginning of collection well 115. Collection well 115 being formed by sides 113A, 113B, 113C and a portion of side 109B. Shoulder 114A connects side 109A to side 113A and shoulder 114B connects side 109C to side 113B. The bottom of bin 107 being formed by bottom 117. Thus, as can be seen in operation the robotic arm when extracting medication from bin 107 would pass down along and adjacent to wall 159B down into well 115. As can be seen as dosages of medication are extracted from bin 107 the remaining dosages of medication would then naturally fall towards well 115 until the bin is empty. If for some reason the dosages of medication become logged and do not move the bin can be shaken to dislodge them. The shaking mechanisms have been disclosed above with each bin having its own shaking mechanism in the embodiment shown.

Bin 107 can also be used as a dispensing or delivery bin 29. The only modification being removal of bottom 117 to form an opening at the bottom through which dosages of medication can fall into a container 36, FIGS. 2 and 3, placed below the opening formed by 117 to collect medication dosages as robotic arm deposits them in dispensing or delivery bin 29. Alternatively, bottom 117 can be formed as a remote controlled trap door and opened after the delivery or dispensing bin has been filled and the medication is ready to be dispensed.

The actual dimension of storage bin 107 can be varied within the ambit of the invention disclosed herein. However, in one embodiment the dimensions of bin 107 are as follows: All of the sides of bin 107 have a thickness of 2.77 mm, and it can be constructed, as one skilled in the art can appreciate, of any suitable material, a plastic type of material being one of them. Referring to FIG. 13D top opening of bin 107 has the following dimensions: side 109A is 33.73 mm, side 109B is 10.14 mm, side 109C is 33.73 mm, and side 109D is 32.77 mm Referring to FIG. 12, side 109D is 39.38 mm along the edges that meet side 109A and 109C. Side 109D is 32.77 mm along the side that meets sloping side 111. Collection well has a cubic shape being approximately 10.14 mm along each edge. With these dimensions one skilled in the art can calculate the remaining dimensions of bin 107.

Housing and Method

Figure 14:
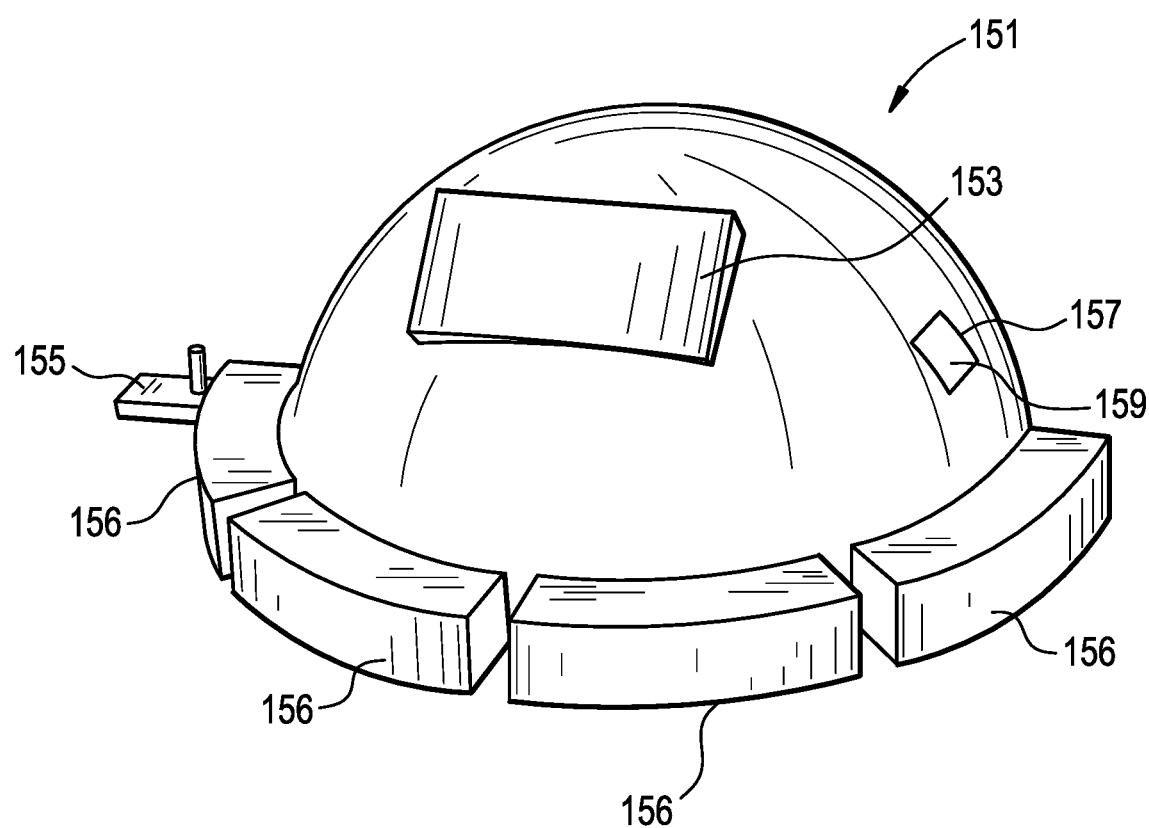
FIG. 14 is a perspective view of an embodiment of a case or enclosure within which the system of the present invention can be housed during use.

FIG. 14 is a prospective view of an embodiment of the housing 151 that would hold and protect the dispensing apparatus. It includes a touch computer screen 153 that provides the graphical user interface, a receptacle area 155 where the medications are dispensed by the dispensing bin and compartments 156 around it side for the storage of medicines such as ointments, inhalers, etc. that cannot be dispensed in tablet, pill, gel, etc. form. 157 is an opening leading to a chute 159 through which dosages of medication are loaded into the various storage bins. As will be discussed in more detail below the bins are loaded through opening 157 and chute 159 by positioning a storage bin below chute 159 and emptying the contents of the proscription container, not shown. The individual loading the medications would instruct the computer to position each storage bin below chute 159 and load the bin by pouring the dosages of medication through opening 157 down chute 159 and enter the necessary information into the computer as noted below.

Figure 15:
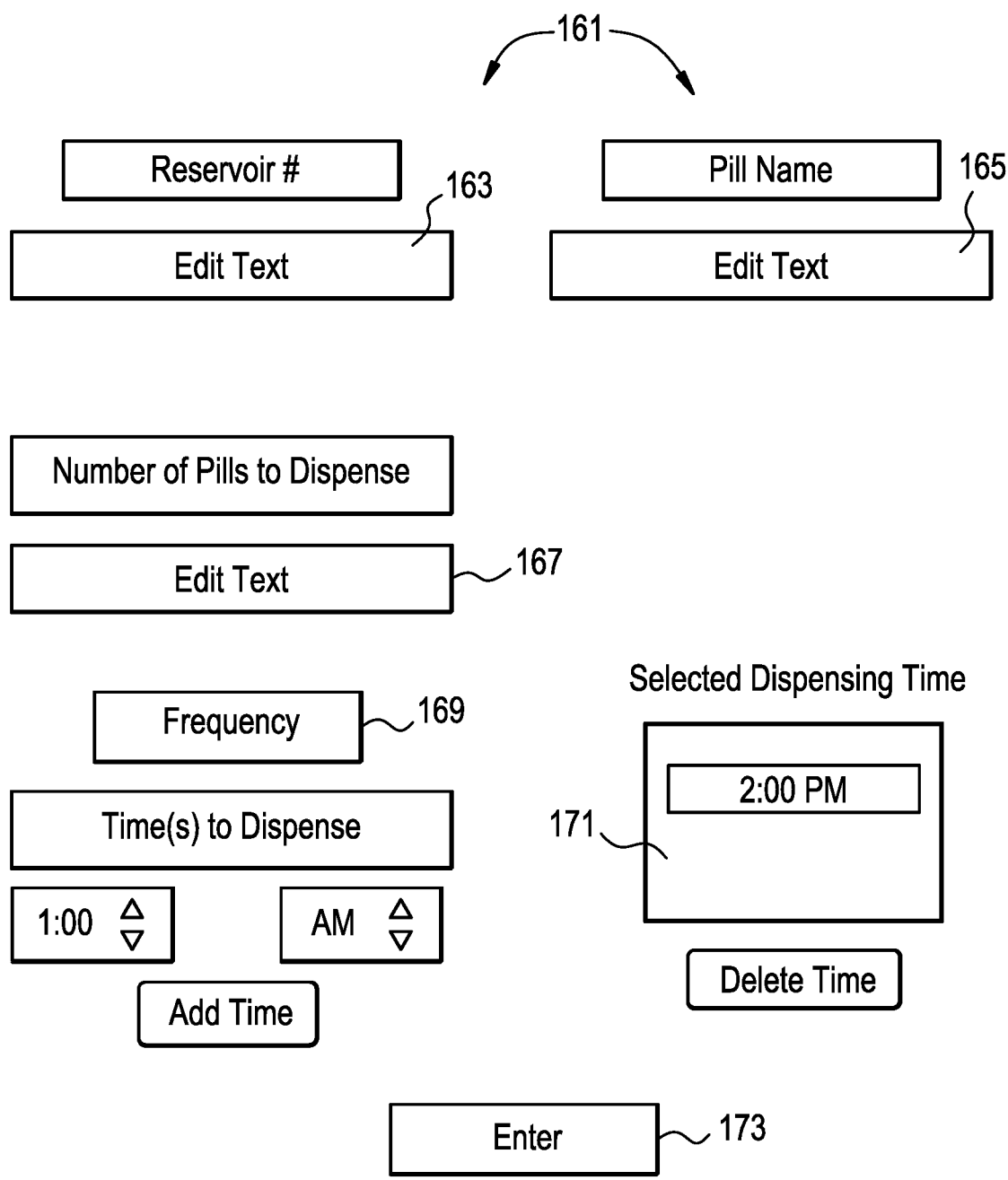
FIG. 15 is a view of an embodiment of the computer screen used for entering information, displaying information and data, and controlling the system.

FIG. 15 is an embodiment of a computer display 161 which would appear on graphical user interface 153. In the embodiment shown it is a touch screen and the user would interact with it by entering the specific storage bin a medication is to be stored in at 163, the identity of the medication at 165, the dosage or number of pills, etc. to be dispensed at 167, the frequency at 169 and the time of day at the particular medication is to be dispensed 171. Once all of the information has been registered it would be saved to the computer by pushing the enter button 173.

Figure 16A:
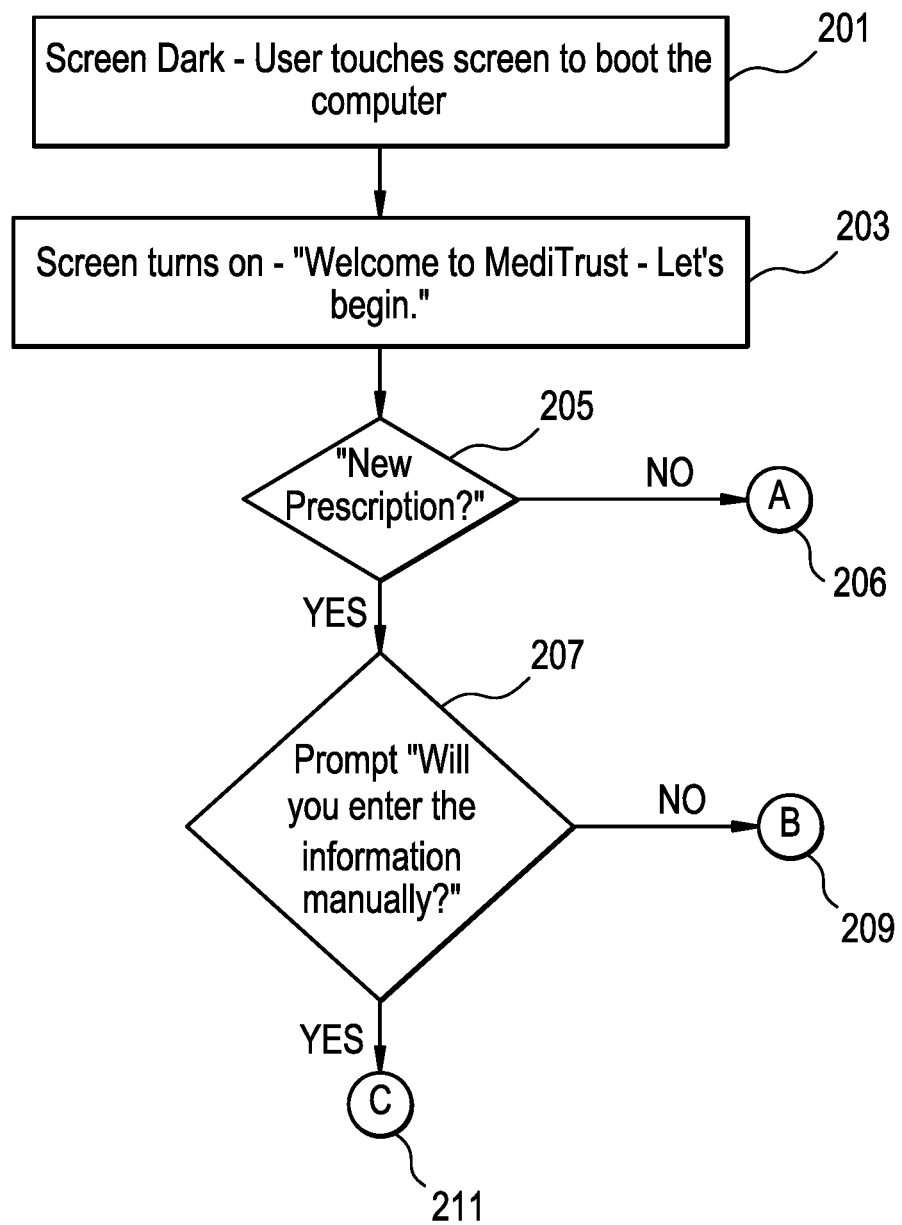
FIG. 16A is a flow chart that shows an embodiment of a portion of the basic system operation when the storage bins are being filled with medication.

FIG. 16A is a flow chart of the initial steps of the basic storage bin loading routine mentioned above. When medication needs to be a placed in the system the user activates the system by tapping the screen 201. The prompt "Welcome to MediTrust— Lets begin" 203 appears on the screen. The computer then asks "New Prescription?" 205. If the user answers "NO" the user is directed to routine A 206. If the user answers "YES" the users is then asked "Will you enter information manually 207?" If the user answers "NO" the users is directed to routine B 209, on the other hand if the answer is "YES" the user is directed to routine C 211.

Figure 16B:
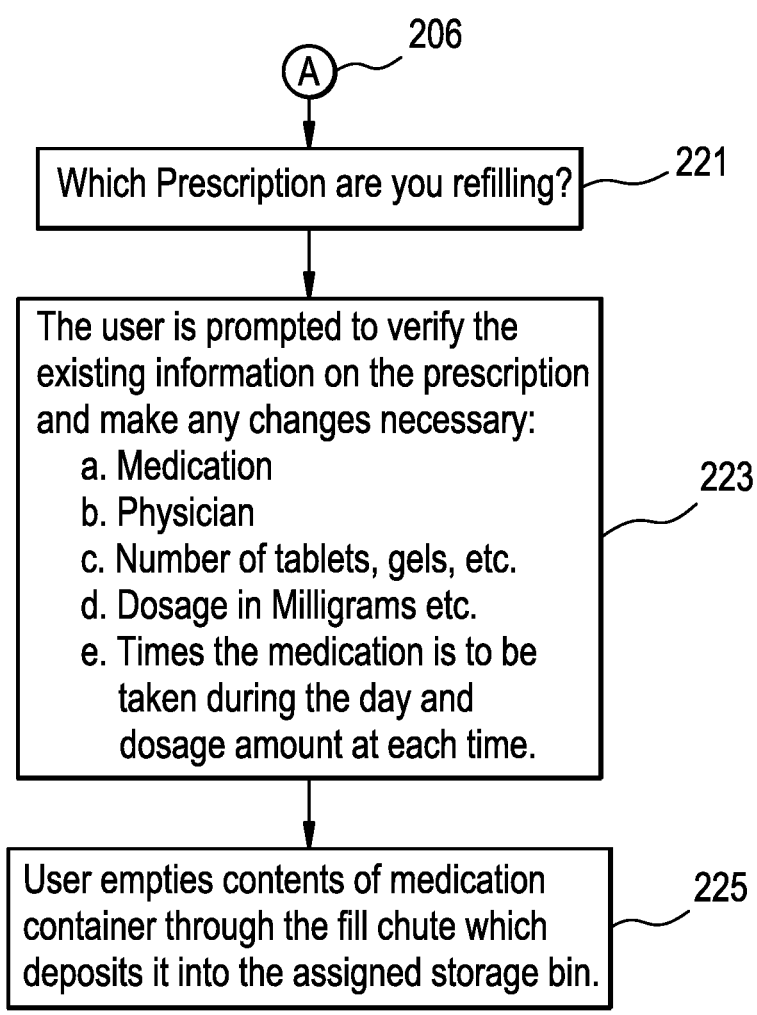
FIG. 16B is a continuation of the flow chart of FIG. 16A.

FIG. 16B sets out the basic steps of routine A 206. Since the system assumes an existing prescription is being filled it will asks the users to identify the existing prescription being refilled 221. Once the existing prescription is identified the system then asks the user to review the existing information on the prescription and make any revisions or changes necessary 223. The information typically being: a) medication, b) prescribing physician, c) number of dosages of medication, d) dosage in milligrams, etc. and e) times the medication is to be taken during the day and dosage mount to be taken. Naturally, any other pertinent information can be included. The final step is to empty the contents of the prescription container into the system 225. The computer will have sent an instruction to place the specific bin which holds that prescription under the loading chute to receive the medication.

Figure 16C:
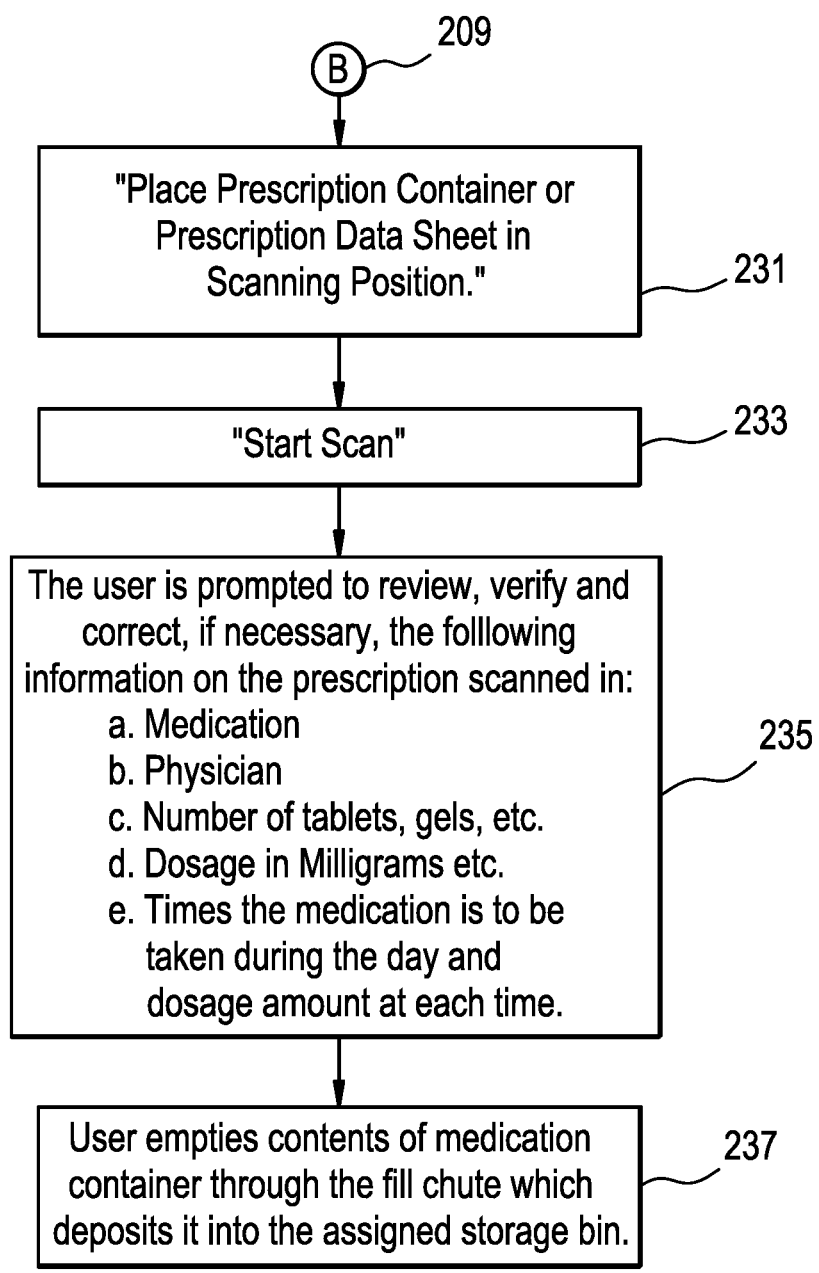
FIG. 16C is a continuation of the flow chart of FIG. 16A.

FIG. 16C sets out the steps of routine B 209. Since the user indicates that they will not be manually entering the information but scanning it in since this is the other alternative the user will be prompted to place the prescription container or prescription data sheet on the scanning holder or in the scanning position 231 and then prompted to start the scanning process 233. Once scanning is completed the computer then displays the information scanned on the computer screen and prompts the user to make any changes, corrections or additions to the information on the prescription 235. The information typically being: a) medication, b) prescribing physician, c) number of dosages of medication, d) dosage in milligrams, etc. and e) times the medication is to be taken during the day and dosage mount to be taken. Naturally, any other pertinent information can be included. The final step being the emptying of the prescription container into the system 237. The computer will have sent an instruction to place the specific bin which will hold that prescription under the loading chute to receive the medication.

Figure 16D:
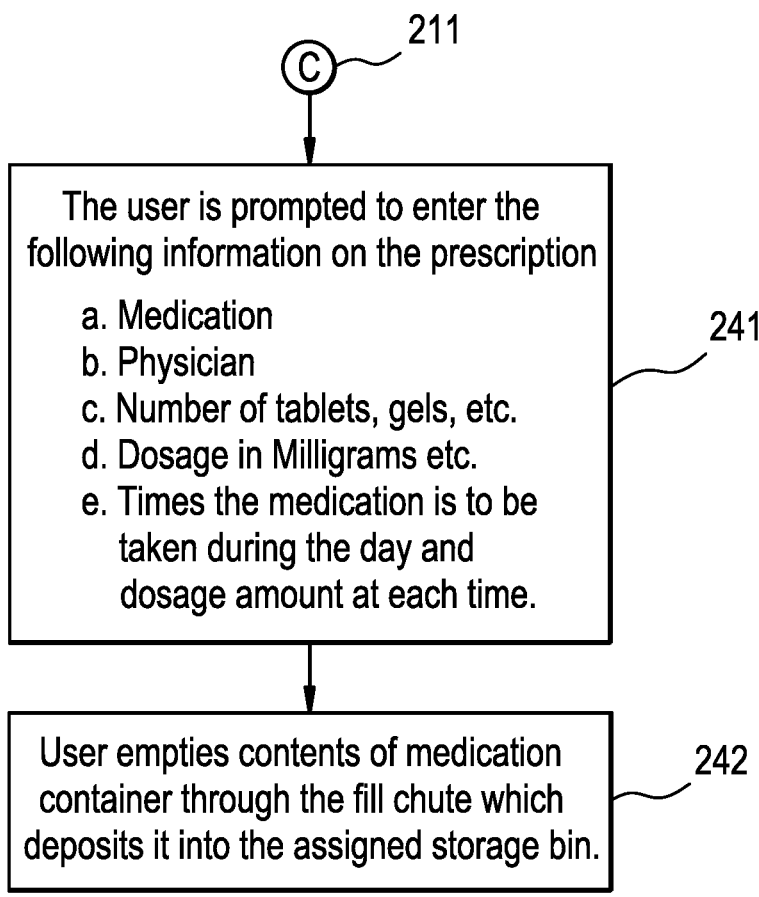
FIG. 16D is a continuation of the flow chart of FIG. 16A.

FIG. 16D sets out the steps of routine C 211. Since the system has been prompted that the information will be entered manually by the user it will them provide a touch keypad on the screen similar to an i-Pad touch keypad. The user will then be prompted to enter the relevant information 241. The information typically being: a) medication, b) prescribing physician, c) number of dosages of medication, d) dosage in milligrams, etc. and e) times the medication is to be taken during the day and dosage mount to be taken. Naturally, any other pertinent information can be included. The final step being the emptying of the prescription container into the system 242. The computer will have sent an instruction to place the specific bin which will hold that prescription under the loading chute to receive the medication.

Figure 17:
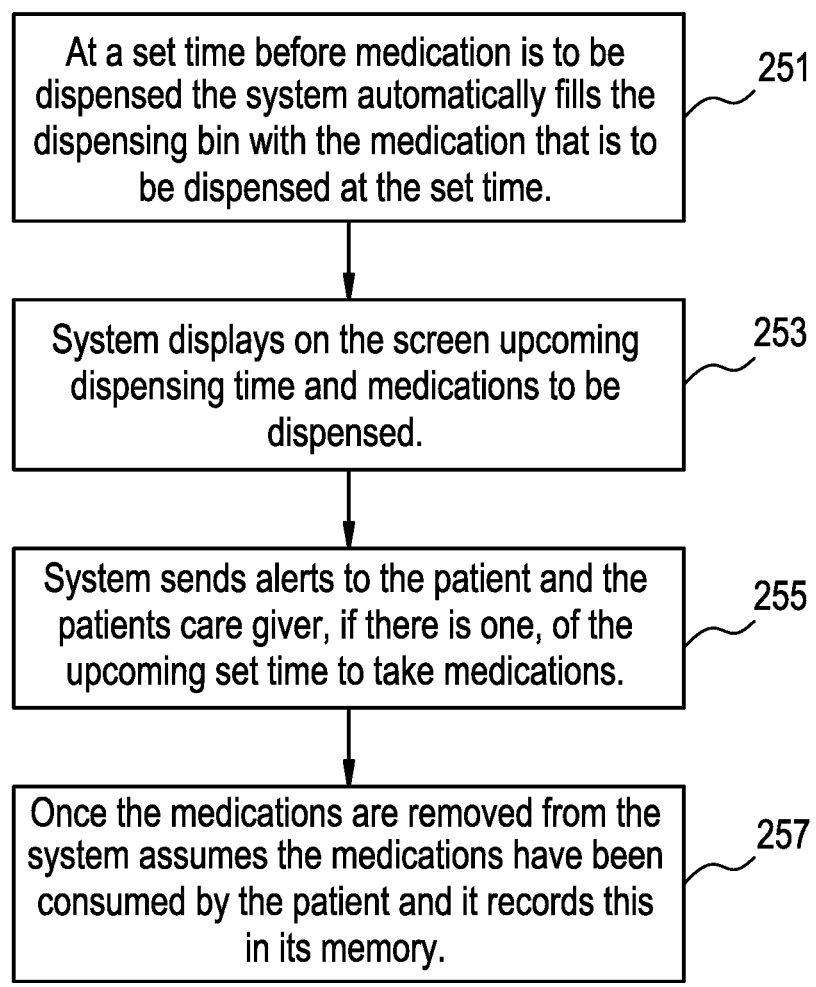
FIG. 17 is a flow chart of an embodiment of basic routine run by the computer to fill the dispensing reservoir for dispensing medication at a preset time.

FIG. 17 is a flow chart of the basic steps for dispensing medication. At a set time before medication is to be dispensed the system automatically fills the dispensing bin with the medication that is to be dispensed at the set time 251. The robotic arm under the control of the computer moves the correct dosage of medication to be dispensed at a preset time from the storage bins to the dispensing bin. The actual time it starts to fill the dispensing bin is one the system operator can set. The only restriction will be that it will have to be after medication has been dispensed at the previous preset time. Typically, it might be 20 minutes to half an hour before the preset time for the medication to be dispensed. The computer displays on its screen the upcoming dispensing time and medications to be dispensed at that preset time 253. Once the dispensing bin is filled an alert is sent to the patient and if appropriate the patent's care giver of the fact the patient needs to take medication at a preset time 255. The system can be programmed to continue to send out alerts until the medication has been taken. The system having a sensor which indicates when the medication to be taken is removed from the system. Once the medications are removed from the system, it assumes the medications have been consumed by the patient and it records this in its memory 257.

The typical prescription container label has most if not all of the information needed in the system of the present invention to program the computer to dispense the medication. Additionally, the pharmacy often provides a separate sheet with most if not all of the information on the prescription container label. This information as noted above is needed to complete programing the computer for proper dispensing of the medication. One of the options discussed above is for someone to manually enter the information through a touch pad screen, 153, FIG. 14. Namely, the medication name, amount of medication, etc. However, as noted above and in FIG. 16c the option of scanning in the image of the prescription container label or information sheet is provided. The computer would be programmed with the necessary optical character recognition software (OCR) and additional software to extract the information on medication, dosage, time and frequency of dispensing to the patient, etc. As noted once this information is extracted it is presented to the person loading the medication into the system for review and correction before it is finalized.

Figure 18A:
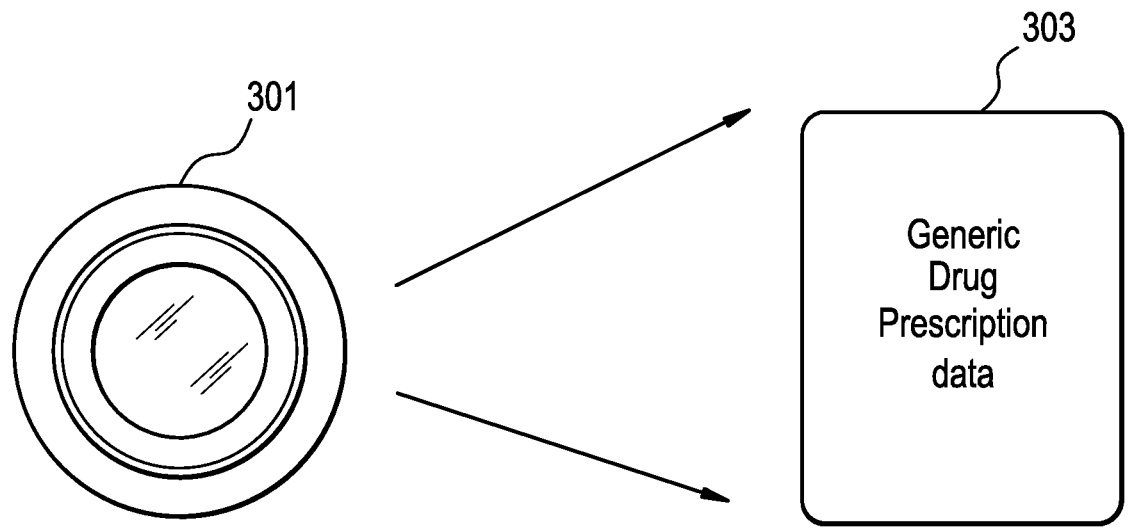
FIG. 18a is a perspective view of an embodiment of an apparatus of the present invention used to scan information from a prescription information sheet into the computer.

FIG. 18a provides a view of an embodiment of a system for scanning in the information from a sheet 303 with the prescription information a sheet provided by the pharmacy with the prescription. Sheet 303 would be imaged in the standard fashion by imaging apparatus 301. Such set ups have been used for years and are well known in the art. The computer programming will include appropriate OCR software well known in the art. The software will identify the information provided and enter the information into the system. Naturally, since this is not a perfect process entry of the information will not be complete until the person loading the system with the medication has reviewed and corrected the information to assure it is accurate.

Figure 18B:
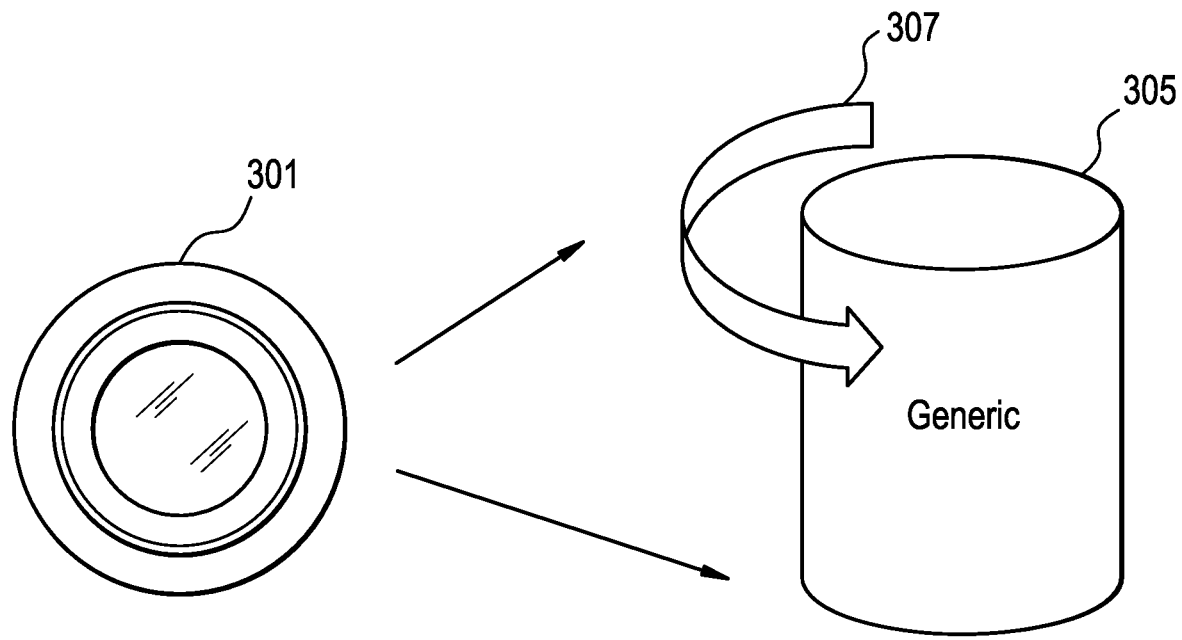
FIG. 18b is a perspective view of an embodiment of an apparatus of the present invention used to scan information from the label of a prescription container into the computer.

FIG. 18b depicts an embodiment of a scanning imaging device 301 the present invention might use to scan information from the prescription bottle label 305. The system includes a scanning or imaging device 301 positioned to scan the label of a prescription container 305 as it is rotated 307. The embodiment of the imaging holder depicted can rotate arrow 307 prescription container with label 305 to allow the complete image of the prescription container label to be captured. Typically most prescriptions come in cylindrical containers. Recent developments in scanning and image recognition technology have developed systems for taking what might be a nonplanar image and restoring it a full planar image to thereby allow OCR extraction of the necessary information.

Another Variation of the Apparatus

Figure 19:
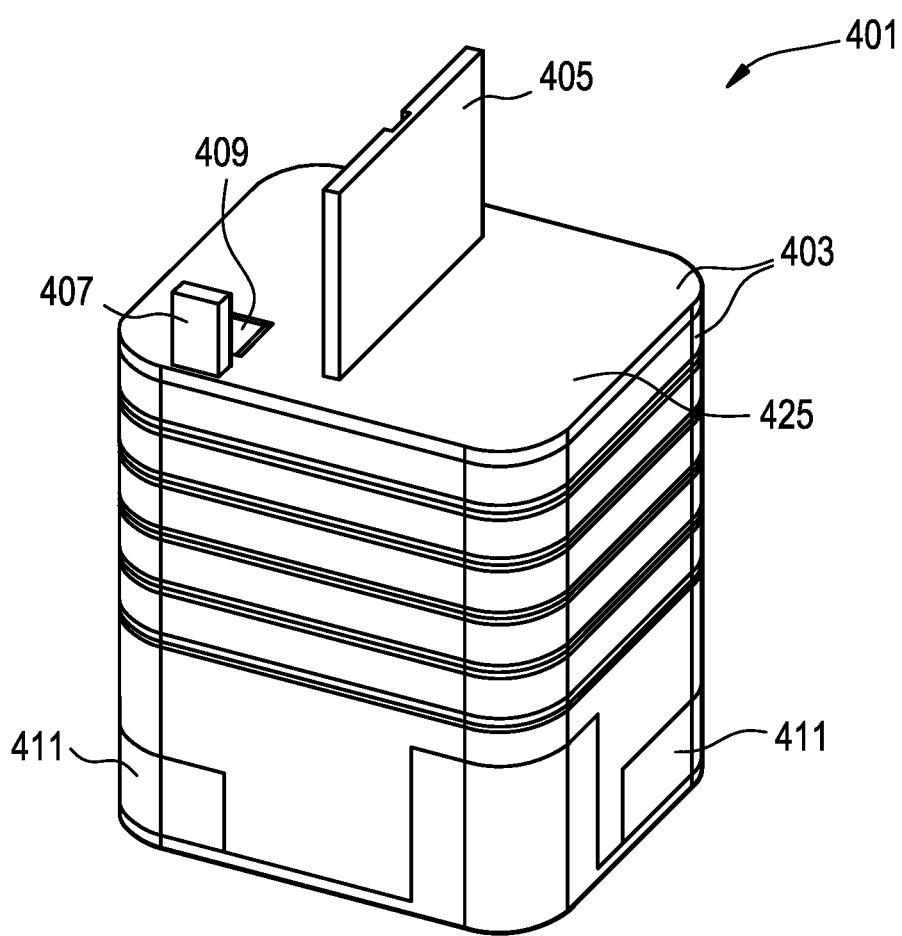
FIG. 19 provides a perspective view of a housing of another variation of the marshalling, storage and dispensing apparatus of the present invention.

FIG. 19 provides a perspective view of another variation 401 of marshalling, storage and dispensing apparatus of the present invention. The variation 401 depicted here has essentially the same function and functionality as that previously discussed. Thus, only the significant differences in mode or function will be discussed in detail. The view depicts only the outside housing 403 and exterior components. The exterior components being screen 405, loading door 407, and a portion of loading slot 409. Screen 405 works in the same fashion as that previously discussed. Bins or compartments 411 to hold and store inhalers, ointments or other types of medicines that do not come in pill, tablet, gel etc. form are included.

Figure 20:
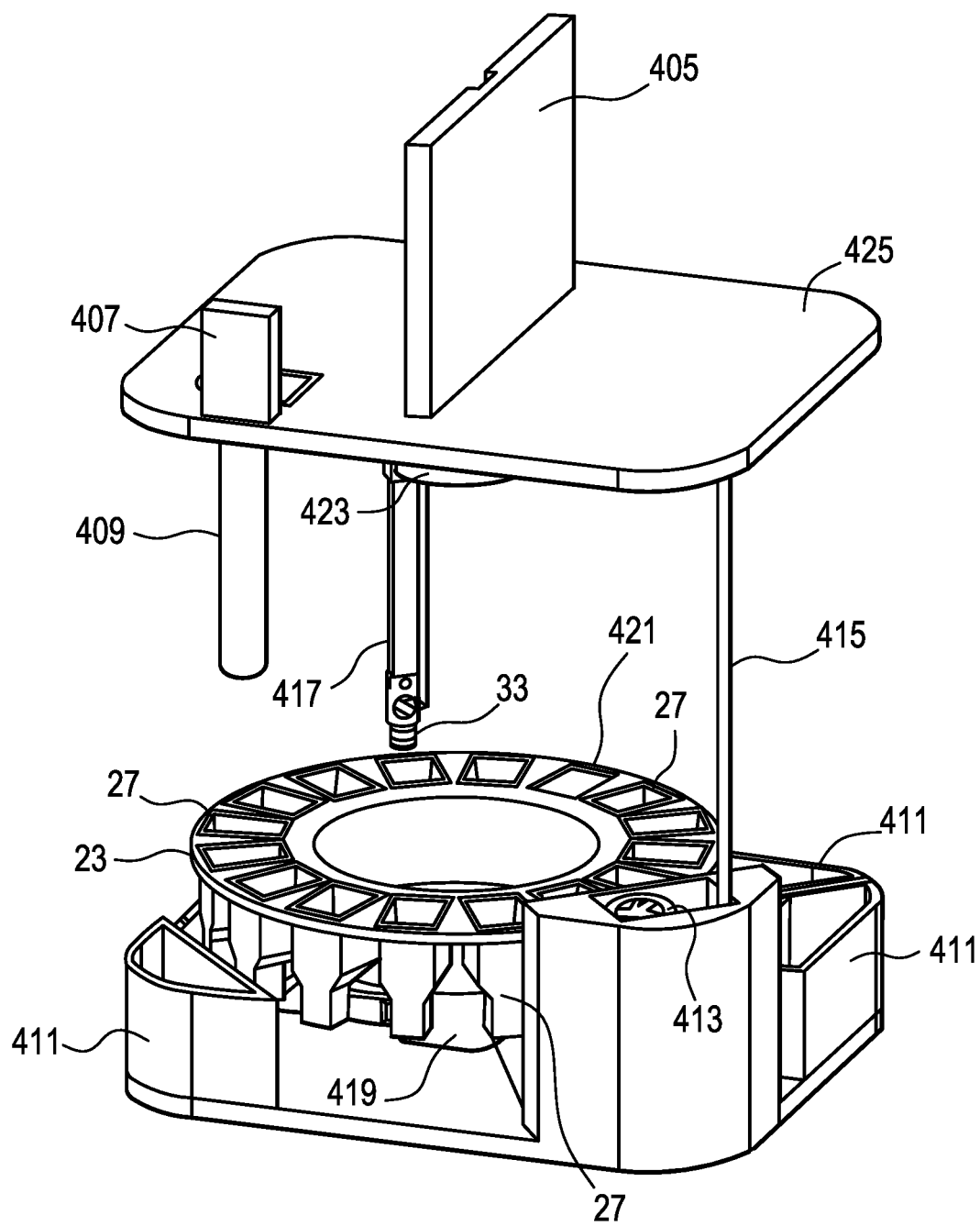
FIG. 20 provides a perspective view of the interior of the variation of the invention depicted in FIG. 19.

FIG. 20 provides a perspective view of the interior mechanism of the variation 401 of the marshalling, storage and dispensing apparatus of FIG. 19. In FIG. 20 a full view of loading chute 409 appears. Visible are vacuum motor 413, vacuum conduit 415, vacuum probe 417, vacuum cup 33, carousel 23, storage bins 27, and actuator 423 a rotary motor and positioner for the vacuum probe. Vacuum system 413 by way of vacuum conduit 415 which extends up to the bottom side of cover 425 and then along its underside to vacuum probe 417 and down the vacuum probe to cup 33 provides the necessary vacuum for vacuum cup 33 to engage and pick up medication in a bin. Actuator or vacuum rotary motor position apparatus 423 moves the probe to the selected bin. Probe 417 consists of telescoping slides moved by a linear motor that enables probe 417 to extend in an upward or downward direction to allow vacuum cup 33 to engage medication located in a bin 27 attached to it, retract back out of the bin, and then move it to the dispensing cup.

Figure 21:
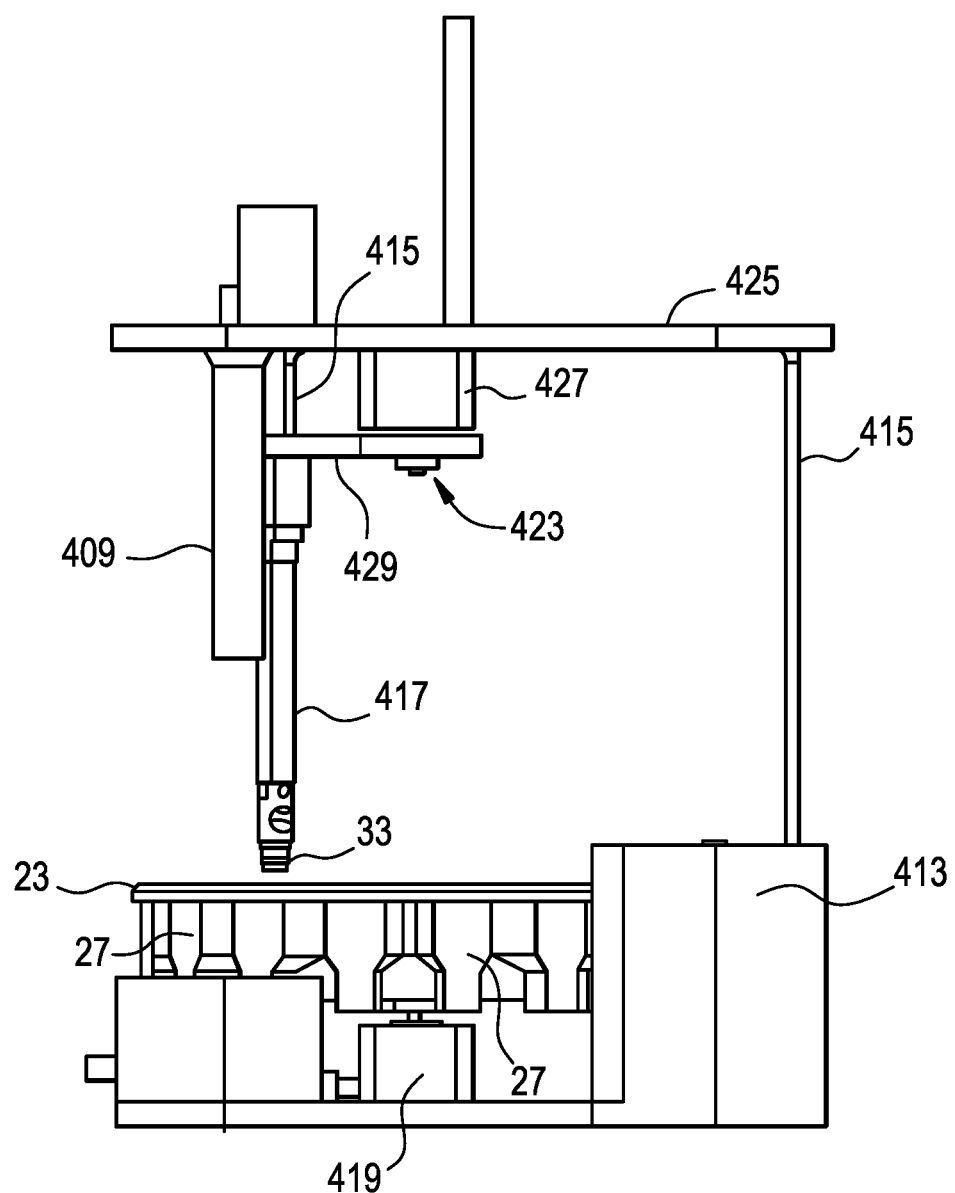
FIG. 21 provides a side view of the variation of the invention depicted in FIG. 19.

FIG. 21 provides a side view of the interior mechanism of the variation 401 of the present invention. Rotary motor 419 is controlled by the computer to turn and position carousel 23. Actuator 423 or vacuum probe rotary motor positioning apparatus consists of rotary motor 427 and arm 429. Rotary motor 427 controlled by a computer, as previously discussed, moves arm 429 in a rotary motion. Vacuum probe 417 connects to the end of arm 429 and movement of arm 429 by rotary motor 427 positions vacuum probe 417 over the selected storage bin 27 from which medication will be extracted and deposited into a dispensing cup.

Figure 22:
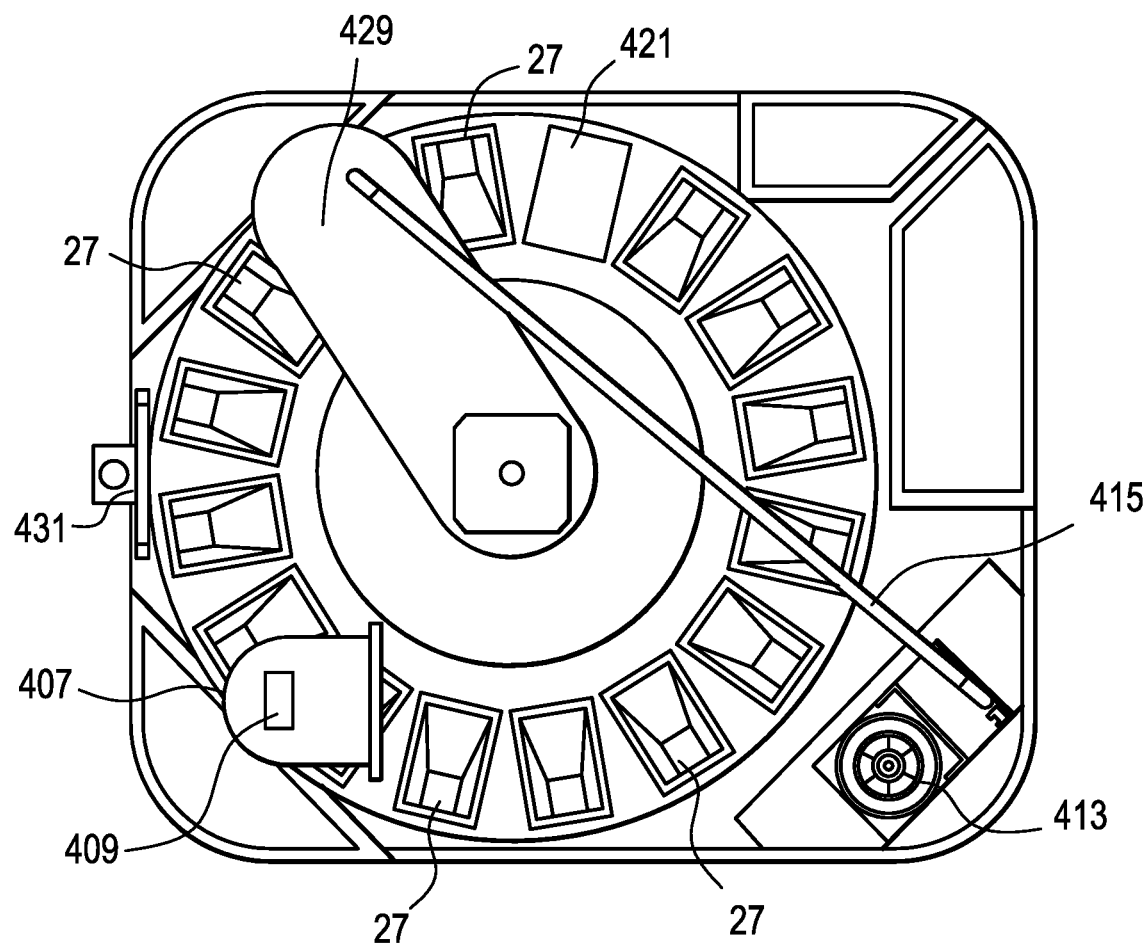
FIG. 22 provides a top view of the interior of the variation of the invention depicted in FIG. 19.

FIG. 22 provides a top view of the interior mechanism of apparatus 401 with cover 425 removed. As the bins 27 are filled with medication, the carousel 23 is rotated to successively place a bin selected for a particular medication under chute 409. One the other hand, when medications are to be dispensed carousel 23 is rotated so that dispensing port 421 is positioned above a dispensing cup located at 431. Arm 429 is then rotated by rotary motor 427 to position it above a storage bin 27 with pre-selected medication. The vacuum probe is then lowered into the storage bin, the medication is then grasped by suction cup 33 and then vacuum probe retracts out of the bin. Rotary arm then turns to position itself over dispensing port 421 positioned above a dispensing cup. The medication is dropped into the dispensing cup. This process continues until the dispensing cup is filled. Once filled, as noted above, a signal is sent reminding the patient and the patient's caregiver that the medication is ready for consumption by the patient.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

It will be apparent to those skilled in the art that various modifications and variations can be made without departing from the spirit or scope of the invention. Since modifications combinations, sub-combinations and variations of the disclosed embodiments incorporating the spirit and substance of the invention may occur to persons skilled in the art, the invention should be construed to include everything within the scope of the appended claims and their equivalents.

What is claimed is:

1. A method for periodically dispensing multiple medications to at least one individual comprising the steps of:
   providing a plurality of storage bins to store dosages of specific medications, each storage bin of said plurality of storage bins being designated to hold only dosages of one specified medication;
   providing a probe with a suction cup at its end wherein said probe with cup at its end can be moved among said storage bins and said probe can grasp a dosage of medication located in any of said storage bins on activation of a pneumatic vacuum system connected to said suction cup and move said probe with said suction cup grasping the dosage to a delivery bin and deposit it in said delivery bin, wherein said suction cup has an articulated body surrounding a hollow interior which is in communication with a vacuum system at an opening at a first end of said suction cup articulated body, and a large lipped surface at a second end, said large lipped surface having an aperture at its center which opens into said hollow interior, said suction cup being made of a soft pliable rubber like material;
   providing a computer system that can be programmed to control and sequence the operation of said probe with said suction cup attached thereto:
   a. move at a preset times with said probe and suction cup predetermined dosages of medication form said storage bins to said delivery bin;
   b. signaling that said delivery bin is filled with the predetermined dosages for consumption by a patient at a preset time;
   c. continuing to send signals that the dosages of medication are ready for consumption until a sensor indicates that the dosages have been removed from said delivery bin;
   d. recording in a memory of said computer the fact the dosages of medication have been removed from said delivery bin;
   e. providing information on dosages of medication dispensed from the delivery bin previously recorded to various care givers and providers; and
   f. periodically conducting a purge cycle to remove particulate matter from said probe and said suction cup;
   programming said computer for loading dosages of medication into predesignated storage bins of said plurality of said storage bins comprising the steps of:
   a. initiating a start of a computer program medication dosage loading routine;
   b. indicating whether the dosages of medication to be loaded are for a new prescription, or an existing prescription already stored in a specific predesignated storage bin;
   c. running the following subprogram if the prescription has been indicated to be an existing prescription already stored in a specific predesignated storage bin:
      i. reviewing information on said existing prescription in said computer system;
      ii. making any corrections to the information in the computer system on the selected existing prescription; and
      iii. verifying the correctness of the information after step c. ii above is completed;
      iv. depositing the new dosages of mediation of the existing prescription in said specific predesignated storage bin;
   d. running the following subprogram if said prescription is new:
      i. designating an available empty storage bin from among said multiple of said storage bins as the storage bin into which the dosages of the new prescription will be stored in;
      entering the information regarding the new prescription into said computer system;
      iii. confirming the information regarding the new prescription is correct; and
      iv. depositing the dosages of mediation of the new prescription into said predesignated storage bin for the new prescription.

2. The method of claim 1 wherein the step of entering information regarding the new prescription is selected from a group consisting of: manually entering the information on the prescription via a computer touch screen, scanning in the image of the prescription information from a label or sheet with the prescription information on it.

3. The method of claim 1 wherein the step of entering the prescription information is the step of entering the following information regarding the prescription: 1) name of the medication, 2) prescribing physician, 3) number of dosages being inserted into said specific storage bin, 4) amount of medication in each dosage, and 5) time at which the medication is to be taken and the amount of dosage to be taken.

\* \* \* \* \*